US012569555B2

(12) United States Patent
Duroux et al.

(10) Patent No.: US 12,569,555 B2

(45) **Date of Patent: *Mar. 10, 2026**

(54) ORGANICALLY MODIFIED MINERAL MICRO-PARTICLES, METHODS OF PREPARING THE SAME AND USES THEREOF

(71) Applicant: Croda International Plc, Goole (GB)

(72) Inventors: Laurent Duroux, Bronshoj (DK); Erik Lindblad, Frederiksberg (DK)

(73) Assignee: Croda International Plc, Goole (GB)

( * ) Notice: Subject to any disclaimer, the term of this patent is extended or adjusted under 35 U.S.C. 154(b) by 1158 days.

This patent is subject to a terminal disclaimer.

(21) Appl. No.: 17/044,769

(22) PCT Filed: Apr. 10, 2019

(86) PCT No.: PCT/EP2019/059118

§ 371 (c)(1), (2) Date: Oct. 1, 2020

(87) PCT Pub. No.: WO2019/201710

PCT Pub. Date: Oct. 24, 2019

(65) Prior Publication Data

US 2021/0106681 A1 Apr. 15, 2021

(30) Foreign Application Priority Data

Apr. 16, 2018 (EP) .................................... 18167434

(51) Int. Cl.

*A61K 39/39* (2006.01)
*A61K 39/00* (2006.01)

(Continued)

(52) U.S. Cl.

CPC ............ *A61K 39/39* (2013.01); *C01B 25/327* (2013.01); *C01B 25/36* (2013.01); *A61K 2039/55511* (2013.01)

(58) Field of Classification Search

None

See application file for complete search history.

(56) References Cited

U.S. PATENT DOCUMENTS 7,550,567 B2 6/2009 Metzner et al.
8,377,909 B2 2/2013 Freixedas et al.

(Continued)

FOREIGN PATENT DOCUMENTS

JP 2004522764 A 7/2004
JP 2005239719 A 9/2005

(Continued)

OTHER PUBLICATIONS

Muthurania et al., Investigation of the sedimentation behavior of aluminum phosphate: influence of pH, ionic strength and model antigens. Journal of Pharmaceutical sciences, vol. 104(11), 3770-3781. Nov. 2015. (Year: 2015).*

(Continued)

*Primary Examiner* — Lakshmi S Channavajjala

(74) *Attorney, Agent, or Firm* — Buchanan Ingersoll & Rooney PC

(57) ABSTRACT

The present invention is situated in the field of mineral micro-particles selected from the list consisting of aluminum hydroxide, aluminum phosphate, amorphous aluminium hydroxyphosphate and calcium phosphate micro-particles. More particularly, the invention provides organically-derivatized mineral micro-particles, uses thereof, and methods of preparing the same.

10 Claims, 20 Drawing Sheets

(51) Int. Cl.
*C01B 25/32* (2006.01)
*C01B 25/36* (2006.01)

(56) References Cited

U.S. PATENT DOCUMENTS

| | | | | |
|---|---|---|---|---|
| 11,554,128 | B2 * | 1/2023 | Duroux | A61K 31/6615 |
| 2010/0092572 | A1 | 4/2010 | Kaeuper et al. | |
| 2014/0314653 | A1 | 10/2014 | Thiriot et al. | |

FOREIGN PATENT DOCUMENTS

| | | | |
|---|---|---|---|
| JP | 2008200476 | A | 9/2008 |
| JP | 2009508472 | A | 9/2008 |
| WO | 02066005 | A1 | 8/2002 |
| WO | 2007022053 | A2 | 2/2007 |
| WO | 2018069520 | A1 | 4/2018 |

OTHER PUBLICATIONS

Gupta et al. Production and Preclinical Evaluation of Plasmodium Falciparum MSP-$1_{19}$ and MSP-$3_{11}$ Chimeric Protein, PfMSP-$Fu_{24}$,Clinical and Vaccine Immunology, 2014, vol. 21, No. 6, pp. 886-897.
Russian Office Action for Application No. 2021136778/04, dated Apr. 28, 2022 with translation, 20 pages.
Belikov V.G., Farmatsevticheskaya khimiya (Pharmaceutical Chemistry). Chapter 2.6 "Relationship between chemical structure, properties of substances, and their effects on the organism" with translation.—M.: MEDpress—inform, 2007, pp. 27-29.
Eisenreich et al., "Adsorption of Inorganic and Organic Phosphorus by Amorphous Aluminum Hydroxide", Journal of Environmental Science & Health Part A: Environmental Science and Engineering, 1978, vol. 13, Nos. 5-6, pp. 337-364.
Onoda et al., "Preparation of Various Aluminum Orthophosphates and Condensed Phosphates and Their Catalytic Properties", Multidiscipline Modeling In Materials and Structures, 2006, vol. 2, No. 4, pp. 463-470.
"Adjuvants in Vaccines for Human Use", PharmAdvisor, 2017, downloaded at https://pharmadvisor.ru/document/tr3685 Introduction and Scope, 4 pages.
Russian Office Action for Russian Application No. 2020136778/04(067793), dated Dec. 27, 2021, 12 pages (English translation).
Hansen et al., "Relationship between the strength of antigen adsorption to an aluminum-containing adjuvant and the Immune response", Vaccine, 2007, 25, pp. 6618-6624.
Jensen et al. "On the effect of Al(OH)3 as an immunological adjuvant" APMIS, 1988, 96, pp. 257-264.
Li et al., "Aluminum hydroxide nanoparticles show a stronger vaccine adjuvant activity than traditional aluminum hydroxide micro-particles", J. Control. Release, Jan. 10, 2014, 173, pp. 148-157.
Li et al., "Peptide vaccine: progress and challenges", Vaccines, 2014, 2(3), 515-536.
Martin R.B., "The chemistry of aluminum as related to biology and medicine", Clinical Chemistry, 1986, 32, pp. 1797-1806.
Woods et al., "Amazing stability of the arginine-phosphate electrostatic interaction", Journal of Proteome Research, 2005, 4(4), pp. 1397-1402.
International Search Report and Written Opinion for International Application PCT/EP2019/059118, dated Jun. 3, 2019, 10 pages.
Guan et al., "ATR-FTIR investigation on the complexation of myo-inositol hexaphosphate with aluminum hydroxide", Journal of Colloid and Interface Science, Academic Press, Inc, US, vol. 293, No. 2, Jan. 15, 2006 (Jan. 15, 2006), pp. 296-302.
Shang et al., "Kinetics of Adsorption of Organic and Inorganic Phosphates by Short-range Ordered Precipitate of Aluminum", Canadian Journal of Soil Science, vol. 70, No. 3, Aug. 1, 1990, pp. 461-470.
Burrell et al., "Aluminium phosphate adjuvants prepared by precipitation at constant pH. Part I: composition and structure", Vaccine, 2000, pp. 275-281.
Burrell et al., "Aluminium phosphate adjuvants prepared by precipitation at constant pH. Part II: physicochemical properties", Vaccine, 2000, pp. 282-287.
Fokkens et al., "A molecular tweezer for lysine and arginine", Journal of the American Chemical Society, 2005, pp. 14415-14421.
Jiang et al., "Structure and adsorption properties of commercial calcium phosphate adjuvant", Vaccine, 2004, 23:693-698.
Lindblad, E., "Aluminum compounds for use in vaccines", Immunology and Cell Biology, 2004,82:497-505.
Mavri et al., "Ion pair formation of phosphorylated amino acids and lysine and arginine side chains: A theoretical study", Proteins Structure Function and Genetics, 24, 1996, pp. 495-501.
Morefield et al., "Role of aluminum-containing adjuvants in antigen internalization by dendritic cells in vitro", Vaccine, 2005, pp. 1588-1595.
Schug et al., "Noncovalent binding between guanidinium and anionic groups: focus on biological- and synthetic-based arginine/guanidinium interactions with phosph[on]ate and sulf[on]ate residues", Chemical Reviews, 2005, pp. 67-113.
Shirodkar et al., "Aluminum compounds used as adjuvants in vaccines", Pharmaceutical Research, 1990, 7:1282-1288.
Wanning et al., "Pharmaceutical spray freeze drying", International Journal of Pharmaceutics, 2015, 488:136-153.
Xiao-Hong et al., "Competitive adsorption between orthophosphate and other phosphates on aluminum hydroxide", Soil Science, Williams and Wilkins Co., Baltimore, US, vol. 170, No. 5, Jan. 1, 2005 (Jan. 1, 2005), pp. 340-349.
Yan et al., : "Mechanism of Myo-inositol Hexakisphosphate Sorption on Amorphous Aluminum Hydroxide: Spectroscopic Evidence for Rapid Surface Precipitation", Environmental Science & Technology, vol. 48, No. 12, May 29, 2014 (May 29, 2014), pp. 6735-6742.
Guan et al., "Competitive Adsorption between Orthophosphate and Other Phosphates on Aluminum Hydroxide", Soil Science, May 2005, vol. 170(5), pp. 340-349.
Ganesan et al., "Calcium Phosphate Nanoparticles as Nuclei for the Preparation of Colloidal Calcium Phytate", New Journal of Chemistry, 2008, vol. 32, pp. 1326-1330.
Japanese Notice of Reasons for Refusal for Japanese Application No. 2020-556795, dated Feb. 7, 2023 with translation, 10 pages.
Konishi et al., "Surface modification of alpha-tricalcium phosphate with inositol phosphate for cement fabrication," Frontiers in Bioengineering and Biotechnology Conference Abstract: 10th World Biomaterials Congress, Mar. 30, 2016, 1 page, doi: 10.3389/conf.FBIOE.2016.01.01851.
Australian Examination Report for Application No. 2019256582, dated Oct. 31, 2023, 5 pages.

* cited by examiner $-P_i = -OPO_3$ $-\mathbf{nP}_{org}$ = organically modified polyphosphate

ORGANICALLY MODIFIED MINERAL MICRO-PARTICLES, METHODS OF PREPARING THE SAME AND USES THEREOF

CROSS REFERENCE TO RELATED APPLICATIONS

This application is the National Stage filing of International Application No. PCT/EP2019/059118, filed Apr. 10, 2019, and claims priority to EP 18167434.2, filed Apr. 16, 2018, both of which are incorporated herein by reference for all purposes.

TECHNICAL FIELD

The present invention is situated in the field of mineral micro-particles consisting of aluminum hydroxide, aluminum phosphate or calcium phosphate or mixtures thereof, for use as a biomolecules delivery or adsorption system such as for use as vaccine adjuvants. More particularly, the invention provides organically-derivatized aluminum hydroxide, aluminum phosphate, or calcium phosphate micro-particles, uses thereof, and methods of preparing the same.

BACKGROUND OF THE INVENTION

Mineral adjuvants, such as aluminum-containing adjuvants, including aluminum phosphate, aluminum hydroxide and calcium phosphate, have been used successfully for decades to enhance the immune response against killed, inactivated and subunit vaccine antigens. Aluminum adjuvants are, at present, the most widely used adjuvants in both veterinary and human vaccines. This has created a great interest in making these mineral-containing adjuvants even more potent. More potent adjuvants and vaccines mean potentially simplified and reduced vaccination campaigns, which is a way to potentially reduce strain on patients, healthcare staff and improve cost/benefits.

A critical aspect of adjuvants potency relies on the delivery and presentation of antigens to the cellular or humoral branches of the immune system in the draining lymph node. The amount or load of antigen adsorbed by the adjuvant (expressed as weight to weight ratio) is one important parameter as it conditions the probability that some of the antigen molecules, together with the adjuvant, will be recognized as foreign material and elicit an appropriate immune response. Achieving higher doses of antigen per units of adjuvants is potentially desirable, as it allows for reduction of the adjuvant loads for the same dose of antigen, which could reduce costs of manufacturing. The strength and the nature of binding of the antigen to the adjuvant is another important parameter as it conditions the probability for the antigen to be presented in particulate form (bound to adjuvant particles) instead of being released in free form into the surrounding physiological environment. This might be particularly relevant for small soluble peptides with high diffusion constants, as a matter of fact peptides as vaccines are generally known to elicit poor immunogenicity and need to be adjuvanted (Li, W., Joshi, M. D., Singhania, S., Ramsey, K. H., & Murthy, A. K. (2014). Peptide vaccine: progress and challenges. Vaccines, 2(3), 515-536.]. A relatively strong binding to the particles will reduce the possibility for the antigen to desorb and to diffuse into the medium, and escape recognition by antigen presenting cells, therefore limiting the potency of the vaccine. However, studies have shown that a too strong adsorption of antigens to the aluminum adjuvants could result in a decrease in vaccine efficiency due to a poor processing and presentation of the adsorbed antigens by the antigen presenting cells (Hansen B. et al., Relationship between the strength of antigen adsorption to an aluminum-containing adjuvant and the immune response, Vaccine, 2007). Thus, there is a strong pressure in the vaccine community and industry to better control the way antigens are ultimately delivered in combination with adjuvants. A possible key to this problem is to be able to design adjuvants tailored to the physico-chemical specificities of the antigen which is to be delivered.

Another aspect of the adjuvant potency might be related to particle size. For example, it has been shown by Morefield et al. (Morefield G. L. et al., Role of aluminum-containing adjuvants in antigen internalization by dendritic cells in vitro, Vaccine, 2005) and Li et al. (Li X. et al., Aluminum hydroxide nanoparticles show a stronger vaccine adjuvant activity than traditional aluminum hydroxide micro-particles, J. Control. Release, 2014) that smaller-sized aluminum-containing particles perform better compared to larger particles, in particular for inducing antigen-specific antibody responses, as smaller particles can be transported to the nearest afferent lymph nodes. At present, there are many techniques available to reduce particle size, such as sonication, high pressure shearing, filtration, homogenization, milling, microfluidization, precipitation or recrystallization. Furthermore, synthesis protocols which result in production of particles of defined size are well established. Adjustment of synthesis parameters, such as the stoichiometric ratio of $Al^{3+}$ and $PO_4^{3}$ (or OH) and pH, can potentially lead to particles of different size (Burrell L. S. et al., Aluminium phosphate adjuvants prepared by precipitation at constant pH. Part I: composition and structure, Vaccine, 2000; Burrell L. S. et al., Aluminium phosphate adjuvants prepared by precipitation at constant pH. Part II: physicochemical properties, Vaccine, 2000).

However, there remains a need for improved methods which are less time consuming and costly, which provide a better control over particle size homogeneity, and which give rise to mineral micro-particles with optimal antigen binding properties.

SUMMARY OF THE INVENTION

In co-pending international application PCT/EP2017/076232, the present inventors describe how stirring a suspension of mineral micro-particles of certain di- or trivalent metal salts selected from aluminum phosphate, amorphous aluminium hydroxyphosphate and/or calcium phosphate, or mixtures thereof, in an aqueous solution of one or more inorganic polyphosphates, such as a solution of an organic polyphosphate, brings about a modification of said mineral micro-particles, which leads to both a significant change of their nominal electrostatic potential and to a decrease in particle size. Without being bound by theory, it is assumed that these modifications are caused by a substitution reaction, or ligand exchange, of hydroxide or orthophosphate groups by inorganic polyphosphate ions at the surface of said mineral micro-particles.

The present inventors have now found that a similar substitution reaction, or ligand exchange, can be achieved using organic polyphosphates of the general formula 1A or 1B:

Formula 1A

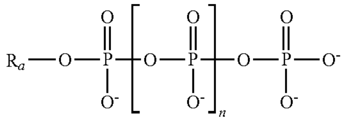

Formula 1B

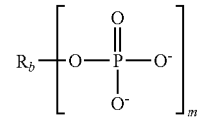

wherein n is an integer in the range of 0-5 and m is an integer in the range of 2-10, and wherein Ra denotes organic substituents selected from adenosine and other nucleosides, thiamines, carbohydrates and isoprenes, and Rb denotes organic substituents selected from inositols and other cyclitols, and carbohydrates.

The organic polyphosphates according to the present invention can thus be deemed "polyphosphates" by virtue of either carrying at least one polyphosphate group $—O—PO_2—(—O—PO_2—)_n—O—PO_3$, in which n is an integer in the range of 0-5, or carrying between two and ten phosphate groups, $—O—PO_3$.

As examples of organic polyphosphates of Formula 1A can be mentioned adenosine and other nucleoside phosphates such as ATP and ADP, thiamine phosphates such as thiamine triphosphate and -diphosphate, Carbohydrate polyphosphates such as α-D-ribose 5-triphosphate and L-Ascorbic acid-2-triphosphate, Pterin phosphates and Isoprenoid phosphates such as Geranyl diphosphate.

As examples of organic polyphosphates of Formula 1B can be mentioned inositol-and other cyclitol phosphates such as inositol bisphosphate (IP2), inositol trisphosphate (IP3), inositol tetraphosphate (IP4), inositol pentakisphosphate (IP5) and inositol hexaphosphate (IP6) also known as phytic acid, or phytate (as a salt). Further examples of Formula 1B include carbohydrate phosphates such as glucose 1,6-bisphosphate, fructose 1,6-bisphosphate, fructose 2,6-bisphosphate, ribulose-1,5-bisphosphat, 2-deoxy-D-ribose 1,5-bisphosphate, and 1,3- and 2,3-diphosphoglycerate.

The present invention as disclosed herein provides surprising advantages in comparison with the disclosure of co-pending international application PCT/EP2017/076232. Using organic polyphosphates of the general formula 1A or 1B lead to enhanced reaction yields at the particle surface, which results in higher surface coverage. As a consequence, a more significant change of the nominal electrostatic potential of the micro-particles is observed than previously, and controlling the decrease in particle size appears to be easier, as the stability of the resulting smaller organically-derivatized mineral micro-and nanoparticles seems to be higher. Secondly, and most importantly, using organic polyphosphates especially of the general formula 1B leads to a higher thermal stability of the final modified mineral micro-particle than can be achieved with the inorganic polyphosphates described in co-pending international application PCT/EP2017/076232, which is important for autoclavation/sterilization purposes. Finally, the adsorption capacity towards antigens, as exemplified by the model antigen hen-egg lysozyme (HEL), of the organically-derivatized mineral microparticles according to the present invention is higher than observed for the inorganic polyphosphate-modified microparticles disclosed in co-pending international application PCT/EP2017/076232. The inventors believe that this is likely caused by a chelating effect of positively charged residues in proteins and polypeptides, such as Lysine and Arginine, by the organic polyphosphates of the general formula 1B in particular, resulting in stronger adsorption to the surface of the particles.

Organic polyphosphates of the general formula 1A may have a lower thermal stability than the polyphosphates of the general formula 1B. Nucleotides (exemplary of Organic polyphosphates of the general formula 1A) are biological multifunctional molecules which play a central role in energy metabolism, DNA synthesis and cellular signaling. They consist of a nucleoside moiety with a mono-, di- or tri-phosphate group at the 5'-position of the ose moiety. Because of the affinity of phosphates for aluminium gels, nucleotides such as ATP adsorb to aluminium adjuvants, and can therefore be used to modify the adjuvant particles surface electrostatic potential. Likewise, adjuvant aluminium particles can be used to carry and deliver nucleotides to cells. However, aluminium adjuvants are typically sterilized by autoclave, which is not compatible with the chemical integrity of nucleotides. In conditions of high temperature and pressure met in autoclaving, hydrolysis of the phosphoric anhydride bonds of the inorganic polyphosphate chain of ADP or ATP will occur, and the physical and chemical properties of these molecules be lost or modified adversely. As alternative to autoclaving, solutions of concentrated ATP, ADP or AMP, up to 100 mM in water, can be filter sterilized through a membrane with 0.22 μm or 0.10 μm pores, and the sterilized solutions fed to the autoclaved aluminium adjuvant particles to the appropriate final concentration, e.g. from 0.5 mM to 2 mM, thereby obviating the need for autoclaving.

The reaction with organic polyphosphates of Formula 1A or Formula 1B has been performed with certain di- or trivalent metal salts selected from aluminum phosphate, aluminum hydroxide, amorphous aluminium hydroxyphosphate and/or calcium phosphate, but is applicable to a wide range of other mineral micro-particles.

The substitution reaction, or ligand exchange, may be performed within a wide temperature range which is compatible with an aqueous reaction environment.

Throughout the present application the term "unmodified mineral microparticle" shall refer to the starting material for said substitution reaction/ligand exchange, whereas the term "organically-derivatized mineral microparticle" shall refer to the result, or product, of said substitution reaction/ligand exchange.

FIG. 6A shows the assumed reaction between an mineral microparticle starting material (here: aluminum phosphate) with a solution of an organic polyphosphate, which takes place at the surface of the microparticle. Aluminum phosphate as referred to in the present context (adjuvants) is essentially aluminum hydroxy-phosphate in which some of the hydroxyl groups (AI-OH) have been replaced by orthophosphate groups ($Al—OPO_3$, denoted Pi). The reaction occurs primarily between the available Al—OH groups and dissolved organic polyphosphate ions, and results over time in a gradually more complete coverage of the aluminum phosphate particle surface with organic polyphosphate groups (denoted nPorg). The substitution reaction presumably also involves orthophosphate groups; i.e. such that available orthophosphate groups to some degree are replaced by organic polyphosphate groups. It is however assumed that hydroxy groups are better leaving groups than orthophosphate groups and therefore are preferentially substituted.

The mineral micro-particle starting material is in fact composed of clusters/aggregates of smaller crystallites, as observed with electronic microscopy in FIG. 6C. It is assumed that the crystallites are held together at least in part by hydrogen bonds between the hydroxy-groups located on the particles. Once the hydroxy groups start to be exchanged by organic polyphosphate groups, the reduced number of hydrogen bonds weakens the cohesion of the crystallites. At the same time, the growing number of closely located organic polyphosphate groups with their multiple negative charge lead to a further destabilization of the crystallite cluster and its eventual de-aggregation (FIG. 6B), as observed with electronic microscopy (FIG. 6C).

However, in comparison with the inorganic polyphosphate-modified mineral micro-particles described in co-pending international application PCT/EP2017/076232, the stability of the resulting organically-derivatized mineral micro-particles of the present invention is improved. First, the phospho-ester bond in molecule of the type 1B presents a much higher activation energy than the phosphoric acid anhydride bond between two orthophosphates (general formula 1A), which results in the possibility to perform heat treatment for sterilization without hydrolyzing most of the phosphate groups and therefore preserving the properties of the modification with such organic polyphosphates. Second, and without being bound by theory, the inventors believe that increased stability of the particles in suspension (colloid) is caused at least in part by the increasing steric hindrance imposed by the organic phosphate groups which have attached themselves to the surface of the mineral micro-particle. The organic residue (Ra or Rb) of the organic phosphate groups are much bulkier than the inorganic polyphosphate ions discussed in PCT/EP2017/076232. Therefore, after some of the original hydroxy- or orthophosphate groups situated on the surface of the mineral micro-particles have been substituted by organic polyphosphate groups, the access to the remaining hydroxy- or orthophosphate groups becomes effectively blocked towards further substitution.

Additionally, the present inventors have found that the organically-derivatized mineral micro-particles have increased binding properties for positively-charged biomolecules, or biomolecules with patches of positive charges, more particularly antigen-binding properties. This property is presumably caused by an increased attraction of positively-charged biomolecules, such as antigens, to the surface of said organically-derivatized mineral micro-particles, leading to an increased adsorption capacity and/or binding strength, i.e. an increased association constant. In view hereof, the organically-derivatized mineral micro-particles according to the present invention can, for instance, be used as improved vaccine adjuvants.

Accordingly, in a first aspect there is provided herein a method for preparing organically-derivatized mineral micro-particles which comprises stirring a suspension of the mineral micro-particle starting material in a solution of one or more organic polyphosphates, wherein said mineral micro-particles are selected from aluminum phosphate, aluminum hydroxide, amorphous aluminium hydroxy-phosphate and/or calcium phosphate micro-particles, or mixtures thereof, and wherein said organic polyphosphate is selected from compounds of formula 1A or 1B:

Formula 1A

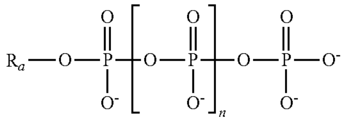

-continued

Formula 1B

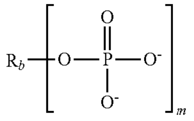

wherein n is an integer in the range of 0-5 and m is an integer in the range of 2-10, and wherein Ra denotes organic substituents selected from adenosine and other nucleosides, thiamines, carbohydrates and isoprenes, and Rb denotes organic substituents selected from inositols and other cyclitols, and carbohydrates.

The stirring is continued for a duration of time which is sufficient to allow a reaction to take place at the surface of the mineral micro-particle by which available hydroxide and to some degree also orthophosphate groups are exchanged, i.e, substituted by organic polyphosphate ions. The substitution reaction may be allowed to proceed for a shorter or longer duration to bring about a partial or more complete substitution of ions.

The aforesaid chemical reaction can be described as a ligand exchange or substitution reaction whereby hydroxide anions located at the surface of the mineral micro-particle starting material are exchanged by organic polyphosphate ions. As the phosphate groups in the organic polyphosphate ions have a much higher affinity for Al (III) than hydroxide, the equilibrium is shifted to the right (for example: ADJU-PHOS®+nPorg-→ADJU-PHOS®-nPorg+OH), according to Le Chateliers principle.

The ligand exchange/substitution reaction, as described above typically takes place in an aqueous reaction environment, and can be carried out within a temperature range from about 0 to about 100 degrees Celsius (° C.), such as for example between 5 to 95° C., or from between 10-90° C., or from between 15-85° C., or from between 20-80° C., or from between 25-75° C., or from between 30-70° C., or from between 40-60° C. The reaction may conveniently be carried out at ambient temperature, or at about 20° C.±5-10° C. The substitution reaction, or ligand exchange may also be carried out under a moderate pressure at temperatures above >100° C.

During the ligand exchange/substitution reaction, the size of the particles is reduced when compared to the size of the original (unmodified) particles. The size reduction depends on how far the substitution reaction has been allowed to proceed, on the reaction rates and the duration of the reaction. The reaction rates are complex as they depend on parameters such as the specific starting material, the type of organic polyphosphate, the initial concentration of organic polyphosphates, the pH of the bulk solvent, the reaction temperature and interfacial effects (at the interface of the particle surface and the bulk solvent).

The progress of the reaction can be followed either on-line by in situ measurement, or off-line by sampling and subsequent analysis of the isolated sample. The skilled person will thus require no inventive effort to establish the correct reaction period for a certain combination of a mineral micro-particle starting material with organic polyphosphates. For example, the use of ion chromatography would allow to quantify the amount of organic polyphosphate ions disappearing from the bulk solution as a function of time, and give an indirect measurement of the amount of such ions being adsorbed at the surface of aluminium phosphate or calcium phosphate particles. Alternatively, direct measurement of organic polyphosphate ions adsorption to the surface of particles could be measured by sensitive electrochemical methods such as electrochemical scanning tunneling microscopy (STM), electrochemical quartz crystal admittance (EQCA), or even by detecting changes in mass using a sensitive quartz crystal microbalance (QCM). Changes in electro-kinetic potential (zeta-potential) of the particles would also reflect the adsorption of polyphosphates at the Helmholtz plane of the particles surface, according to the electrical double-layer theory.

A relevant monitoring procedure for the ligand exchange/substitution reaction described hereinabove thus involves monitoring the change in zeta-potential as a function of time, or as a function of concentration of the organic polyphosphate, as chemical modifications of the particle surface will be reflected by the surface electrostatic charge with high sensitivity. Complementary methods to monitor the modification of the particle surface include, but are not limited to, Raman Scattering and Infra-Red Absorption spectroscopy which would detect specific chemical signatures of the adsorbed organic polyphosphate, Secondary Ion Mass Spectroscopy which would monitor secondary ions (from organic polyphosphates) desorbed from the particle surface upon irradiation with ion beams, or elemental analysis such as Energy Dispersive X-ray Scattering to record the presence of Carbon from the modifier in particles initially devoid of Carbon. The ligand exchange/substitution reaction may be stopped once a desired zeta value is reached by removing the organically-derivatized mineral micro-particles from the solution of the organic polyphosphate and rinse them in water. The reaction may alternatively be stopped once the zeta-potential does not change by more than 10%, preferably at most 5% over a period of 5-10 minutes, such as 5 minutes, 7.5 minutes or 10 minutes.

For convenience, the ligand exchange/substitution reaction involving mineral micro-particles in a solution of an organic polyphosphate described hereinabove will in the following, and throughout the present patent application, be referred to as an "equilibration" or "equilibration step".

In a second aspect the present invention provides organically-derivatized mineral micro-particles which are obtainable by the equilibration method according to the first aspect.

In particular embodiments, said equilibration leads to a partial or complete substitution of the phosphate ions or hydroxide ions which are located at the surface of the micro-particles by organic polyphosphate ions.

In other particular embodiments, said equilibration is carried out with organic polyphosphate ions of the general structure 1A.

In preferred embodiments, said equilibration is carried out with organic polyphosphate ions of the general structure 1B.

In a particularly preferred embodiment, said equilibration is carried out with phytic acid/IP-6/inositol-hexaphosphate or a salt thereof.

In particular embodiments, said equilibration of said mineral micro-particles with an organic polyphosphate increases the nominal electrostatic potential of said mineral micro-particles.

In particular embodiments, said equilibration of said mineral micro-particles with an organic polyphosphate decreases the size of said mineral micro-particles.

In particular embodiments, said solution of an organic polyphosphate comprises a negatively charged salt of the organic polyphosphate, preferably wherein said solution has a physiological pH.

In another embodiment, said solution of an organic polyphosphate comprises a mixture of two or more negatively charged organic polyphosphate salts.

In particularly preferred embodiments, said solution of an organic polyphosphate comprises inositol hexaphosphate (Phytic acid/IP-6).

In other particular embodiments, said equilibration step is performed i. at ambient temperature, or at about 20° C.±5-10° C.,
ii. over a reaction period of at least 2 minutes, and/or
iii. with an initial concentration of organic polyphosphates of at least 0.1 mM and at most 20 mM, and/or
iv. at pH values comprised between pH 4.0 and pH 7.5

In particular embodiments, said mineral micro-particle starting material has i. a nominal size of at least 0.1 μm and at most 5 μm when measured in colloidal suspension by DLS or laser diffraction, and/or
ii. a zeta-potential of at least −20 and at most −30 mV for aluminum phosphate, when measured at pH 7.0 in distilled water.
iii. a zeta-potential of at least +10 and at most +20 mV for aluminum hydroxide, when measured at pH 7.0 in distilled water.
iv. a zeta-potential of at least −10 and at most −20 mV for calcium phosphate, when measured at pH 7.0 in distilled water.

Also provided herein are organically-derivatized mineral micro-particles prepared by equilibration of mineral micro-particles selected from the list consisting of aluminum hydroxide micro-particles, aluminum phosphate micro-particles, amorphous aluminium hydroxyphosphate and/or calcium phosphate micro-particles, wherein at least part of the hydroxide ions located at the surface of said mineral micro-particles are substituted by organic polyphosphate ions.

In particular embodiments, the organically-derivatized mineral micro-particles according to the invention have (i) a nominal zeta-potential of at least −35 mV, for aluminum phosphate, when measured at pH 7.0 in distilled water,
(ii) a zeta-potential of at least +10 and at most +20 mV for aluminum hydroxide, when measured at pH 7.0 in distilled water.
(iii) a nominal zeta-potential of at least −40 mV, for calcium phosphate, when measured at pH 7.0 in distilled water,
(iv) a nominal size of at least 0.01 μm and at most 2 μm,
(v) a stoichiometric ratio of Al to P of 1.2+/−0.15 to 1,
(vi) a stoichiometric ratio of Ca to P of 1.7+/−0.2 and/or
(vii) a maximum surface coverage of said micro-particles by organic polyphosphate ions leading to a maximal stochiometric ratio nPorg/Al of 0.05.

In other particular embodiments, the organically-derivatized mineral micro-particles are provided as a slurry or suspension in a sterilized, saline buffered aqueous solution.

In yet other particular embodiments, the organically-derivatized mineral micro-particles are provided as a spray freeze-dried powder (Wanning et al., Pharmaceutical spray freeze drying. International Journal of Pharmaceutics, 2015, 488:136-153), ready for reconstitution in sterile water.

In yet another particular embodiment, the organically-derivatized mineral micro-particles are provided as a dry, lyophilized formulation optionally containing trehalose as a stabilizing excipient.

In particular embodiments, said organically-derivatized mineral micro-particles according to the invention have increased biomolecule-binding properties compared to the mineral micro-particle starting material, preferably wherein said biomolecule has an opposite charge than said modified micro-particle or wherein said biomolecule is neutral when said modified micro-particle is neutral. In particular embodiments, said biomolecule is an antigen.

Also provided herein is the use in medicine of said organically-derivatized mineral micro-particles according to the invention.

In particular embodiments, said organically-derivatized mineral micro-particles according to the invention are used as biomolecules delivery or adsorption systems.

In particular embodiments, said biomolecules delivery system is a vaccine adjuvant.

In particular embodiments, said organically-derivatized mineral micro-particles according to the invention are used as vaccine adjuvants in vaccines.

In particular embodiments, said organically-derivatized mineral micro-particles according to the invention are used in blood fractionation, preferably as biomolecules adsorption systems.

BRIEF DESCRIPTION OF THE FIGURES

FIG. 1 shows the amounts of HEL adsorbed to ADJU-PHOS® particles as a function of the concentration of HEL in the suspensions. Clearly, the treatment of ADJU-PHOS® particles with IP6 improves the adsorption capacity of the particles over the treatment with meta-hexaphosphate (m6Pi), with a maximum capacity of 1.4 mg HEL/mg equivalents $Al^{3+}$ for IP6 in comparison to 1.1 mg HEL/mg equivalents $Al^{3+}$ for m6Pi and ~0.8 mg HEL/mg equivalents $Al^{3+}$ for orthophosphate (Pi). In addition, these results show that the superior HEL adsorption capacity of ADJU-PHOS® particles treated with IP6 is achieved even after autoclaving, used as a sterilization process for Adju-Phos.

FIG. 2 shows the dependency of calcium phosphate particles zeta-potential on the concentration of orthophosphate (Pi), meta-hexaphosphate (m6Pi) and inositol-hexaphosphate (IP6). Treatment with any phosphate lead to an increase in the zeta-potential of calcium phosphate particles, which suggests an adsorption phenomenon of the phosphate ions at the surface of the particles. This dependency of the zeta potential on concentration is reminiscent of a Langmuir-type adsorption isotherm, which would suggest a saturation of binding sites. Whereas ortho-phosphate leads to an increase from about −5 mV to −20 mV, the polyphosphates m6Pi and IP6 show a more dramatic increase in zeta potential to about −50 mV and −60 mV respectively.

FIG. 3 shows the amounts of HEL adsorbed to calcium phosphate particles as a function of the concentration of HEL in the suspensions. Clearly, the treatment of calcium phosphate particles with IP6 improves the adsorption capacity of the particles over the treatment with meta-hexaphosphate, with a maximum capacity of ~180 μg/mg equivalents $Ca^{2+}$ for IP6 in comparison to ~120 μg/mg equivalents $Ca^{2+}$ for m6Pi and ~45 μg/mg equivalents $Ca^{2+}$ for Pi.

FIG. 4 clearly demonstrates how ATP adsorption capacity is increased at least 5-fold over AMP and non-phosphorylated adenosine. It can be concluded that the presence of a condensed triphosphate group in ATP, instead of a monophosphate group in AMP is responsible for this effect. The mechanisms by which the triphosphate group enhances the adsorption capacity of adenosine remains to be investigated. It can be hypothesized that the presence of additional hydroxyl groups on the polyphosphate chain increases statistically the probability of bonding to ADJU-PHOS® via ligand exchange, or that these reactive hydroxyls are less sterically hindered in ATP. Alternatively, the chemical reactivity of the terminal hydroxyl groups on the triphosphate chain of ATP is higher than for AMP, or that the phosphate in cx-position in ATP is made more reactive by the pyrophosphate (phosphates in β- and γ-position) acting as a leaving group.

FIG. 5 shows the same pattern observed with other phosphate and polyphosphate ions, where in a first phase the ζ-potential is increased from −43 mV to −60 mV in response to adsorption of inositol hexaphosphate (IP6) to the surface of ADJU-PHOS® particles and, where in a second phase the ζ-potential is decreased from −60 mV to −35 mV most likely as a result of the increased ionic strength leading to Coulomb screening of the charges and compression of the electrostatic double layer. Thus it appears in this experiment that an optimal balance is reached for a concentration of 5 mM IP6.

FIG. 6*a* shows how mineral micro-particles (exemplified by Aluminum hydroxide) react with an organic polyphosphate to produce organically-derivatized mineral micro-particles wherein some hydroxy-groups have been displaced by organic polyphosphate groups.

FIG. 6B shows how the organically-derivatized mineral micro-particles eventually begin to break up due to (presumably) charge-charge repulsion.

FIG. 6*c* compares the microscopic morphology of non-modified ADJU-PHOS® particles (top picture) to ADJU-PHOS® ZP modified with 2 mM Na-IP6. ADJU-PHOS® particles have an average size distribution of ~2.5 μm and are composed of aggregates of small plate-like crystallites of ~20 nm in size. When treated with IP6, ADJU-PHOS® microscopic particles de-aggregate partially, which is seen on the bottom picture as individual crystallites of ~20 nm.

FIG. 7 shows how ATP adsorption capacity is increased at least 2-fold over AMP and non-phosphorylated adenosine. It can be concluded that the presence of a condensed triphosphate group in ATP, instead of a monophosphate group in AMP is responsible for this effect. The mechanisms by which the triphosphate group enhances the adsorption capacity of adenosine remains to be investigated. It can be hypothesized that the presence of additional hydroxyl groups on the polyphosphate chain increases statistically the probability of bonding to ADJU-PHOS® via ligand exchange, or that these reactive hydroxyls are less sterically hindered in ATP. Alternatively, the chemical reactivity of the terminal hydroxyl groups on the triphosphate chain of ATP is higher than for AMP, or that the phosphate in (x-position in ATP is made more reactive by the pyrophosphate (phosphates in β- and γ-position) acting as a leaving group.

FIG. 8 shows how ATP and AMP, both phosphorylated forms of adenosine adsorb strongly to ALHYDROGEL®, in comparison to the non-phosphorylated adenosine. There is no apparent difference between ATP and AMP adsorption capacity, indicating that the presence of the tri-phosphate chain in ATP does not apparently confer any additional improvement over the mono-phosphate group in AMP. This is in contrast with ADJU-PHOS® where ATP adsorption capacity is higher than AMP adsorption capacity for the same concentration range. Aluminium hydroxide, because of its nature, has a much higher proportion of hydroxide groups (per mole of aluminium) than ADJU-PHOS® (aluminium hydroxy-phosphate) which can undergo a ligand-exchange reaction with phosphates. Therefore, it is expected that ALHYDROGEL® presents a higher adsorption capacity than ADJU-PHOS® for phoshorylated molecules such as ATP or AMP. ALHYDROGEL® reactivity towards AMP and ATP is equal or similar, as it may only involve the terminal phosphate group with little difference in reactivity.

FIG. 9 shows that ADJU-PHOS®ζ-potential increases (in absolute values) from −40 mV to −48 mV with increasing ATP concentration up to 1 mM. Further increase in ATP concentration from 1 mM to 6 mM does not result in further increase in ζ-potential, which indicates that saturation of ATP adsorption sites is reached within 1 mM. In contrast to ATP, treatment with AMP resulted in a decrease in-potential (in absolute values) from −40 mV to −35 mV. This difference between ATP and AMP can be imputed to the higher adsorption capacity of ADJU-PHOS® for ATP than AMP (FIG. 1) and the higher negative charges carried by ATP (tri-phosphate instead of mono-phosphate). No significant changes in ζ-potential were observed for ADJU-PHOS® treated with non-phosphorylated adenosine.

FIG. 10 is a photo of homogenized suspensions in plastic spectrophotometric cuvettes demonstrating the effect of adenosine-5'-triphosphate (ATP) and adenosine-5'-monophosphate (AMP) concentration on ADJU-PHOS® sediment bed-height. ATP concentrations from left to right: 0.0 mM, 0.5 mM, 1.0 mM, 2.0 mM, 3.0 mM, 4.0 mM and 5.0 mM FIG. 11. Effect of adenosine-5'-triphosphate (ATP) and adenosine-5'-monophosphate (AMP) concentration on ADJU-PHOS® sediment bed-height.

FIG. 12 shows that calcium phosphate adsorbs ATP, AMP and adenosine and that adsorption capacity increases as a function of concentration in seemingly linear fashion, with only little sign of saturation (within the range of nucleotide concentrations used in this experiment). ATP and AMP also appear to be adsorbed in higher amounts than adenosine, suggesting that the phosphate groups are the cause of higher adsorption capacity. It can be hypothesized that the presence of phosphate groups in AMP and ATP increases adsorption to calcium phosphate via ligand exchange with hydroxide ions in the calcium phosphate matrix, as the calcium phosphate adjuvant used in this experiment is an (water insoluble) hydrated salt of calcium and phosphate with an unknown stoichiometric number of hydroxides.

FIG. 13 shows that calcium phosphate ζ-potential increases (in absolute values) from −5 mV to −40 mV with increasing ATP concentration up to 1 mM. This sharp increase in-potential is interpreted as specific adsorption to the particles Stern layer (according to the electrostatic double-layer model). Further increase in ATP concentration from 1 mM to 6 mM only results in marginal increase in ζ-potential, which indicates that saturation of ATP adsorption sites is reached within 1 mM. In contrast to ATP, treatment with AMP only results in a slight increase in ζ-potential (in absolute values) from −5 mV to −10 mV, also indicating specific adsorption to the particles surface. As the adsorption capacity of ATP and AMP to calcium phosphate appears similar (FIG. 3), the marked difference in-potential between ATP and AMP can be imputed to the higher negative charge carried by ATP (tri-phosphate instead of mono-phosphate). No significant changes in-potential were observed for calcium phosphate treated with non-phosphorylated adenosine, indicating that no specific adsorption is occurring to the particles Stern layer. This result indicates that the adsorption of adenosine to calcium phosphate (FIG. 3) may be non-specific, resulting of mass transfer and entrapment into the gel matrix. The adsorption of ATP and AMP appears to be specific as the changes in ζ-potential indicates a chemisorption process with a resulting change in the net electrostatic charge of the calcium phosphate particles.

FIG. 15 shows that the bed height of calcium phosphate sediment, measured after 48 hours at rest, decreases as a function of ATP concentration, from 11 mm to 6 mm. The most dramatic decrease in bed-height occurs from 0.0 to 2.0 mM ATP, which corresponds to the concentration range where the calcium phosphate ζ-potential is the most increased (FIG. 13), suggesting that the two parameters are linked. Interestingly, AMP treatment does not modify calcium phosphate sediment bed-height. It appears as if the tri-phosphate chain on adenosine-5'-triphosphate induces a packing of calcium phosphate particles despite the increased ζ-potential, from which electrostatic repulsion forces are expected to keep particles apart from each-other. A similar pattern is observed with inorganic polyphosphates and phytate (inositol-hexaphosphate).

FIG. 16 shows that upon dilution in imidazole 5 mM at pH 7.0, the ζ-potential of untreated ADJU-PHOS® decreases (in absolute values) from −35 mV to −22 mV in a range of dilutions from 5-fold to 320-fold, respectively. In contrast, ADJU-PHOS® initially treated with 0.2 mM Na-IP6 shows higher ζ-potential values from −47 mV to −33 mV, following a trend parallel to that observed for untreated Adju-Phos.

For untreated ADJU-PHOS®, the decrease in-potential as function of dilution could be explained by a reduction in the strength of the electrostatic field, as the average inter-particle distance increases with dilution. This indicates that at low dilution-fold, particles are in close range and, their mutual electrostatic field interacts (overlap) and appears stronger (higher ζ-potential). With increasing dilution, inter-particle distance increases and the apparent electrostatic field strength decreases (lower ζ-potential). This effect is also seen for ADJU-PHOS® ZP. However, the difference in higher ζ-potential between ADJU-PHOS® ZP and ADJU-PHOS® is constant at about −12 mV.

If IP6 was only reversibly adsorbed to ADJU-PHOS®, one would have expected the ζ-potential of ADJU-PHOS® ZP at high dilution-fold to reach that of ADJU-PHOS®, but this is not the case. A dilution of 320-fold from the initial ADJU-PHOS® treated with 0.2 mM IP6 would result in a final IP6 concentration of 0.6 μM. When ADJU-PHOS® is treated with concentrations of IP6 lower than 10 μM, no change in ζ-potential is observed. Therefore, the result shown in FIG. 16 strongly indicates that a fraction of the initial IP6 is strongly adsorbed to ADJU-PHOS® and has modified its ζ-potential irreversibly.

Figure 17:
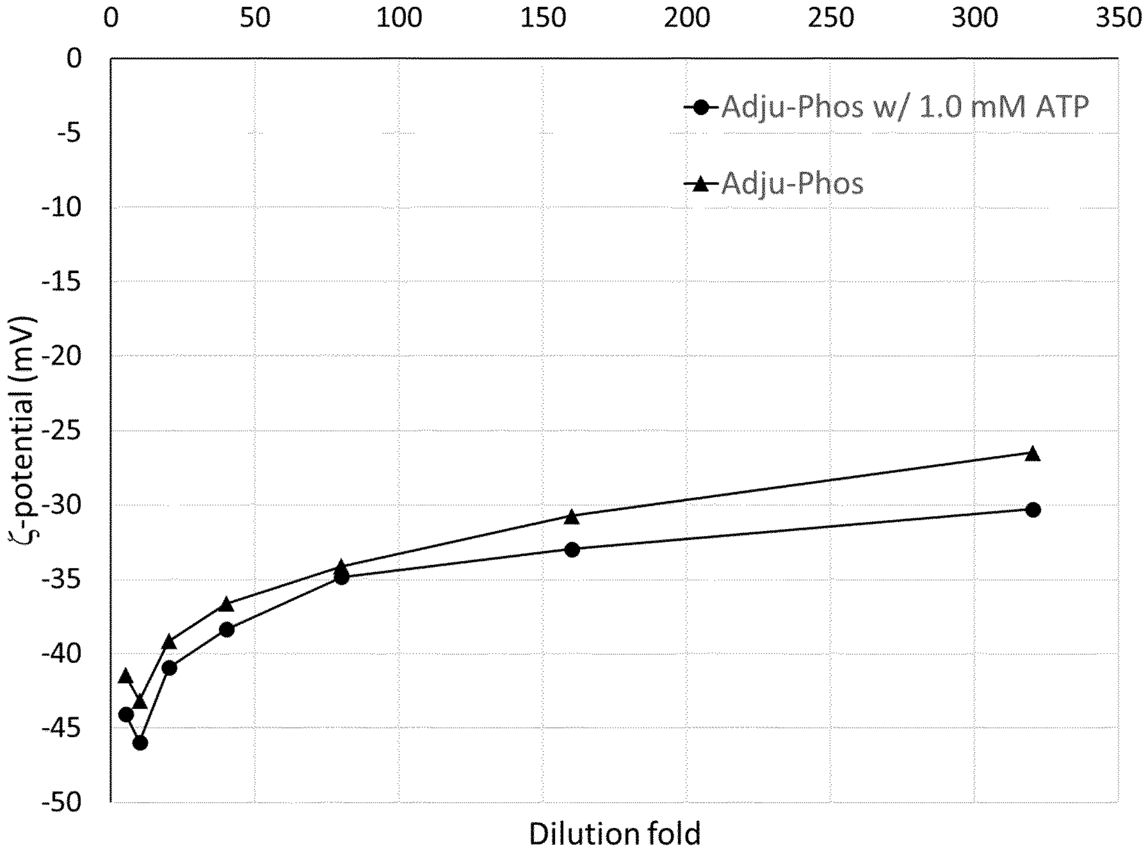

FIG. 17: Effect of serial dilutions of ADJU-PHOS® initially treated with ATP FIG. 17 shows that upon dilution in imidazole 5 mM at pH 7.0, the ζ-potential of regular (untreated) ADJU-PHOS® decreases (in absolute values) from −41 mV to −27 mV in a range of dilutions from 5-fold to 320-fold, respectively. ADJU-PHOS® initially treated with 1.0 mM ATP shows marginally higher-potential values from −44 mV to −30 mV, following a trend parallel to that observed for untreated ADJU-PHOS®.

Compared to the treatment of ADJU-PHOS® with IP6 (Experiment no. 12, FIG. 16), ADJU-PHOS® treated with ATP also shows an increase in ζ-potential irrespective of the dilution-fold, although the difference in ζ-potential is only about −3 mV (compared to −12 mV for IP6). Following the same argumentation than for Experiment no.12, this result is indicative of a strong adsorption of ATP to ADJU-PHOS®.

Figure 18:
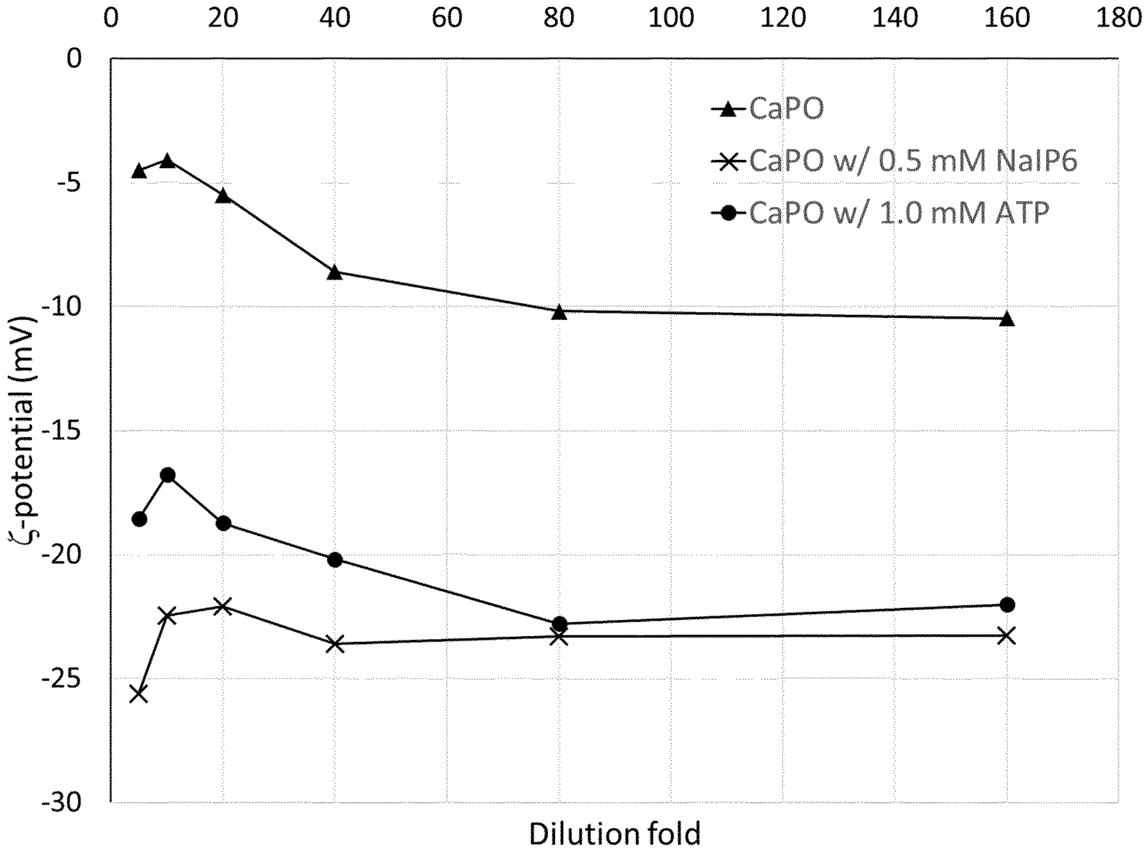

FIG. 18. Effect of serial dilutions of calcium phosphate initially treated with IP6 or ATP.

FIG. 18 shows that upon dilution in imidazole 5 mM at pH 7.0, the ζ-potential of untreated calcium phosphate increases (in absolute values) from −5 mV to −10 mV in a range of dilutions from 5-fold to 320-fold, respectively. In contrast, calcium phosphate initially treated with 0.5 mM Na-IP6 shows higher-potential values from −26 mV to −23 mV. Likewise, calcium phosphate initially treated with 1.0 mM ATP shows higher ζ-potential values from −16 mV to −22 mV.

If IP6 or ATP were only reversibly adsorbed to calcium phosphate, one would have expected the ζ-potential of calcium phosphate at high dilution-fold to reach that of calcium phosphate, but this is not the case. A dilution of 320-fold from the initial calcium phosphate treated with either 0.5 mM IP6 or 1.0 mM ATP would result in a final IP6 concentration of 1.5 μM IP6 or 3.0 μM ATP, respectively. When calcium phosphate is treated with concentrations of IP6 or ATP lower than 10 μM, no change in-potential is observed. Therefore, the result shown in FIG. 18 strongly indicates that a fraction of the initial IP6 or ATP is strongly adsorbed to calcium phosphate and has modified its-potential irreversibly.

DEFINITIONS

Unless defined otherwise, all technical and scientific terms used herein have the same meaning as commonly understood by one of ordinary skill in the art to which this invention belongs. Although any methods and materials similar or equivalent to those described herein may be used in the practice of testing of the present invention, the preferred methods and materials are now described. In this specification and the appended claims, the singular forms “a”, “an”, and “the” include plural references unless the context clearly dictates otherwise.

The terms “comprising”, “comprises” and “comprised of” as used herein are synonymous with “including”, “includes” or “containing”, “contains”, and are inclusive or open-ended and do not exclude additional, non-recited members, elements or method steps.

The terms “comprising”, “comprises” and “comprised of” also include the term “consisting of”.

The term “about” as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier “about” refers is itself also specifically, and preferably, disclosed.

The recitation of numerical ranges by endpoints includes all numbers and fractions subsumed within the respective ranges, as well as the recited endpoints.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to “one embodiment”, “an embodiment” means that a particular feature, structure or characteristic described in connection with the embodiment is included in at least one embodiment of the present invention. Thus, appearances of the phrases “in one embodiment” or “in an embodiment” in various places throughout this specification are not necessarily all referring to the same embodiment, but may. Furthermore, the particular features, structures or characteristics may be combined in any suitable manner, as would be apparent to a person skilled in the art from this disclosure, in one or more embodiments.

The term "aluminum phosphate" as used herein refers to amorphous aluminum hydroxyphosphate (Shirodkar S. et al., Aluminum compounds used as adjuvants in vaccines. Pharmaceutical Research, 1990, 7:1282-1288) in which some of the hydroxyl groups of aluminum hydroxide are replaced by phosphate groups. The disordered, amorphous state is responsible for the high surface area and high adsorptive capacity. It is not a stoichiometric compound and its composition depends on the precipitation recipe and conditions. Preferably, the atomic ratio of Al: P is 1.2±0.15-1.

The surface of aluminum phosphate as referred to herein is composed of Al—OH and Al—$OPO_3$ groups. The iso-electric point (IEP) varies from 9.4 to 4.5 depending on the degree of phosphate substitution. Commercial aluminum phosphate adjuvants have IEP values in the 4.5 to 5.5 range.

The term "aluminum hydroxide" as used herein refers to aluminum oxyhydroxide, which is a crystalline, stoichiometric compound.

The term "calcium phosphate" as used herein refers to non-hydroxyapatite calcium phosphate or a composite material comprising mainly non-hydroxyapatite calcium phosphate. Calcium phosphate may be formulated as $Ca_3(PO_4)_2$ or as non-stoichiometric hydroxyapatite, $Ca_{10-x}$ $(HPO_4)_x$ $(PO_4)_{6-x}$ $(OH)_{2-x}$, wherein x is an integer between 0 and 2(Jiang D. et al., Structure and adsorption properties of commercial calcium phosphate adjuvant, Vaccine, 2004, 23:693-698). For example, calcium phosphate may refer to a composite material consisting of brushite ($CaHPO_4 \cdot 2H_2O$) and calcium phosphate ($Ca_3(PO_4)_2$), which can be formulated as $[Ca_3(PO_4)_2]_x \bullet [CaHPO_4 \bullet 2H_2O]_y$, wherein the amount of calcium phosphate (x) is larger than the amount of brushite (γ), or wherein x>y. More particularly, calcium phosphate may refer to a composite material consisting of brushite ($CaHPO_4 \cdot 2H_2O$) in which the weight ratio of Ca/P is approximately 1.29 and the non-hydroxyapatite form of calcium phosphate ($Ca_3(PO_4)_2$) in which the weight ratio of Ca/P is 1.94. Preferably, the atomic ratio of Ca:P is 1.7±0.2-1.

The term "micro-particles" as used herein refers to particles with a nominal size of at least 0.01 μm and at most 10 μm, at most 5 μm, or at most 2 μm. Starting material micro-particles preferably have a nominal size of at least 0.1 μm and at most 5 μm. Furthermore, when said micro-particle is an aluminum phosphate micro-particle, the starting material micro-particle may have a nominal ζ-potential of at least −10 and at most −20 mV when measured in distilled water.

As used herein, the term Pi or $P_i$ shall mean inorganic phosphate. When the condensed inorganic phosphates are cyclic, an "m" is added (meta), as in m6Pi. For example, di-phosphate=2Pi and meta-hexaphosphate=m6Pi.

As used herein, the term "organic polyphosphate" shall mean an organic molecule substituted either with at least two phosphate groups (—O—$PO_3$) or an organic molecule substituted with at least one polyphosphate group —O—$PO_2$—(—O—$PO_2$—$)_n$—O—$PO_3$, in which n is an integer in the range of 0-5:

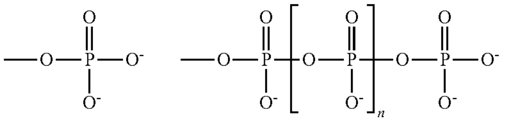

As used herein, the term nPorg shall mean an organic polyphosphate with n=number of phosphate groups.

The term "polyphosphate" as used herein refers to polymers of condensed phosphate, or phosphoric acid, more preferably selected from the list comprising diphosphate, triphosphate, tetraphosphate, pentaphosphate, hexaphosphate, meta-triphosphate, meta-hexaphosphate.

DETAILED DESCRIPTION OF THE INVENTION

The present invention is a further development of an invention disclosed in co-pending international application PCT/EP2017/076232 which relates to the preparation method of modified mineral micro-particles comprising suspending mineral micro-particles of certain di- or trivalent metal salts selected from aluminum phosphate, amorphous aluminium hydroxyphosphate and/or calcium phosphate, or mixtures thereof, in an aqueous solution of one or more inorganic polyphosphates, which brings about a modification of said mineral micro-particles, both in terms of a significant change of their nominal electrostatic potential and to a decreased particle size.

The present invention now discloses organically-derivatized mineral micro-particles comprising aluminum phosphate, amorphous aluminium hydroxyphosphate, aluminum hydroxide and/or calcium phosphate manufactured in a similar fashion by employing a solution of one or more organic polyphosphates, such as a solution of a single organic polyphosphate, in the preparation method. It has been found that the biomolecule-binding properties, preferably wherein said biomolecule is a vaccine antigen, of aluminum phosphate, amorphous aluminium hydroxyphosphate, aluminum hydroxide and/or calcium phosphate micro-particles are improved significantly by treating said micro-particles with organic polyphosphates in comparison to the above-mentioned treatment with inorganic polyphosphates disclosed in co-pending international application PCT/EP2017/076232.

In particular, it was shown that the presumable substitution of phosphate ions or hydroxide ions by organic polyphosphate ions increased the numerical value of the I-potential of said micro-particles, thereby increasing the strength of the electrostatic potential, e.g. for attraction of biomolecules, preferably antigens, and/or the binding strength to the surface of said micro-particles. Furthermore, as disclosed in co-pending international application PCT/EP2017/076232, it has been discovered that the substitution of initial anions in aluminum phosphate, amorphous aluminium hydroxyphosphate, aluminum hydroxide and/or calcium phosphate micro-particles lead to destabilization of the material super-structure and disintegration. As a consequence, treatment of such micro-particles with inorganic polyphosphates results in the reduction of nominal particle size.

It has now been found that the modifications disclosed in co-pending international application PCT/EP2017/076232 can also be achieved with organic polyphosphates as disclosed herein, including the nominal size reduction of aluminum phosphate, amorphous aluminium hydroxyphosphate, aluminum hydroxide and/or calcium phosphate micro-particles.

However, the reactions using organic polyphosphates as disclosed herein are easier to control, especially as regards size reduction, which will be elaborated on elsewhere in the present specification. Moreover, the reaction products using organic polyphosphates as disclosed herein generally have a higher thermal stability than observed for the reaction products using inorganic polyphosphates as disclosed in co-pending international application PCT/EP2017/076232.

The method according to the present invention can conveniently make use of commercially available aluminum phosphate, amorphous aluminium hydroxyphosphate, aluminum hydroxide and/or calcium phosphate micro-particles.

Accordingly, a first aspect of the invention relates to a method for preparing organically-derivatized mineral micro-particles which comprises the step of equilibrating said mineral micro-particles with a solution of one or more organic polyphosphates, such as a solution of a single organic polyphosphate, wherein said mineral micro-particles are selected from the list consisting of aluminum phosphate micro-particles, amorphous aluminium hydroxyphosphate micro-particles, aluminum hydroxide and/or calcium phosphate micro-particles and wherein said organic polyphosphate is selected from compounds of formula 1A or 1B:

Formula 1A

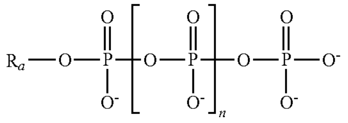

Formula 1B

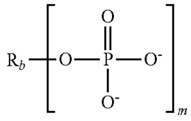

wherein n is an integer in the range of 0-5 and m is an integer in the range of 2-10, and wherein Ra denotes organic substituents selected from adenosine and other nucleosides, thiamines, carbohydrates and isoprenes, and Rb denotes organic substituents selected from inositols and other cyclitols, and carbohydrates.

The reactions of the organic polyphosphates of formula 1A and 1B with mineral micro-particles have been studied individually, and each display significant advantages compared to the analogous reaction with inorganic polyphosphates.

Organic polyphosphates of formula 1A with a short condensed polyphosphate group such as the triphosphates (i.e. for which n=1, exemplified herein by ATP) seem to react much better with the surface hydroxyl groups of Aluminium phosphate particles than does the analogous monophosphate (AMP). Without being bound by theory, the inventors hypothesize that the phosphoanhydride in ATP is more energy-rich and thereby more nucleophilic. The additional negative charges in the ATP vs AMP molecule may be another reason.

Organic polyphosphates of formula 1B are advantageous from the point of view of improving the zeta-potential of the particles, which again lead to an improved antigen-adsorption. This is in particular true for the organic polyphosphates derived from inositols and other cyclitols. Inositol-hexaphosphate (IP6), e.g. has a formal charge of 12 at neutral pH, vs. 6 for hexametaphosphate (m6Pi). The charge density will thus be 100% larger for IP6 than for m6Pi. In addition, it has experimentally been shown that the phospho-ester bond in IP6 is more stable towards hydrolysis than the phospho-anhydride in m6Pi, which indicates that IP6 based adjuvants tolerate autoclavation better than m6Pi based.

In a preferred embodiment, the one or more organic polyphosphates are selected from compounds having the general structure 1B. In a further preferred embodiment, the one or more organic polyphosphates are selected from Inositol-and other cyclitol phosphates in their various isomeric and/or enantiomeric forms, such as inositol bisphosphate (IP2), inositol trisphosphate (IP3), inositol tetraphosphate (IP4), inositol pentakisphosphate (IP5) and inositol hexaphosphate (IP6) also known as phytic acid, or phytate (as a salt).

More preferably, the one or more organic polyphosphates comprises inositol trisphosphate (IP3) or inositol hexaphosphate (IP6).

Most preferably, the invention relates to a method for preparing organically-derivatized mineral micro-particles which comprises the step of equilibrating said mineral micro-particles with a solution of inositol hexaphosphate (IP6) also known as phytic acid, or a salt thereof (a phytate), preferably sodium phytate.

In another preferred embodiment the mineral micro-particles are calcium phosphate micro-particles.

Organically-derivatized micro-particles preferably have a nominal size of at least 0.01 μm and at most 1 μm, preferably from 0.1-0.5 μm, and a nominal ζ-potential as defined elsewhere in the specification. Micro-particles may have various shapes and may be, for example, spherical, conical, ellipsoid, complex-shaped, cylindrical or cubical. Furthermore, micro-particles in a collection of micro-particles may not have all the same size or shape. The term "modified" or "modifying" as used herein refers to altering, amending or making changes, either minor or fundamental, in the form or character of an item, preferably to give rise to an improved (modified) version of said item. For example, organically-derivatized mineral micro-particles as taught herein may have a complete or partial substitution of the phosphate ions or hydroxide ions which are located at the surface of the initial, unmodified micro-particle starting material by organic polyphosphate ions, an alteration in the surface charge, a change in the ζ-potential, a change in the biomolecule-binding and biomolecule adsorption properties and/or a change in the size as compared to the mineral micro-particle starting material before equilibration with a solution of one or more organic polyphosphates. Preferably, said surface charge is numerically higher, said ζ-potential is numerically higher, said biomolecule-binding and biomolecule adsorption properties are increased and/or said nominal size is decreased as compared to the mineral micro-particle starting material before equilibration with a solution of an organic polyphosphate. In preferred embodiments, said biomolecule is an antigen. Furthermore, the organically-derivatized mineral micro-particles may have specific binding sites for chelation of basic amino acid residues at the surface of peptides, proteins, or polypeptides, for instance biomolecules, which are not present in the mineral micro-particle starting material.

In particular embodiments, the equilibration of said mineral micro-particles with a solution of an organic polyphosphate modifies the nominal electrostatic potential of said mineral micro-particles.

The term "electrostatic potential", "electric potential" or "V" as used herein refers to the general meaning of this term as understood by the skilled person, and in particular the potential energy of a charged entity, such as a proton, an electron or an ion at a particular location near a molecule and may be defined as the energy per unit charge (q) (V=U/q). The electrostatic potential may be expressed in units of Joules/Coulomb, or Volts. The electrostatic potential may be used to predict and/or calculate the energies required to move charges from, for example, one potential $V_1$ to another potential $V_2$.

The term "zeta potential" or "ζ-potential" as used herein describes a measure of the relative electrical charge of micro-particles that are suspended in liquid. More particularly, ζ-potential refers to an intermediate electrical potential at a certain distance from a particle's physical surface, the boundary of the so-called diffuse layer (the so-called slipping plane), where ions are in equilibrium between the attractive electrostatic field of the particle surface and the surrounding liquid (e.g. solvent). Accordingly, the ζ-potential describes the electrical potential at a certain distance from a particle's physical surface where the charge of said particle does no longer interfere with the surrounding liquid. The ζ-potential typically ranges from +100 mV to −100 mV and can be measured by using the Zetasizer nano ZS (Malvern Instruments Inc.) in electro-kinetic mode, preferably at 25° C., and/or in deionized water. For micro-particles in a fluid applies that the higher the nominal ζ-potential, the higher the stability in terms of reduced tendency to settle when in suspension. For example, micro-particles with a ζ-potential greater than +25 mV or less than-25 mV typically have a high degree of stability. The modification of the ζ-potential of mineral micro-particles by equilibrating said micro-particles with a solution of an organic polyphosphate, as taught herein can be an increase, a decrease, a reversion and/or neutralization of the ζ-potential of said micro-particles. An increase or decrease of the nominal ζ-potential as taught herein refers to an increase or decrease of the absolute value of the nominal ζ-potential, irrespective of the symbol ((+) or (−)) in front thereof. For example, when the initial nominal ζ-potential is-10 mV, an increase of said nominal ζ-potential may be −15 mV, −20 mV,−25 mV,−30 mv, etc., while a decrease of said nominal ζ-potential may be −5 mV,−3 mV,−1 mV, 0 mV etc. Another example, when the initial nominal ζ-potential is +10 mV, an increase of said nominal ζ-potential may be +15 mV, +25 mV, +50 mV, +100 mV etc., while a decrease of said nominal ζ-potential may be +5 mV, +3 mV, +1 mV, 0 mV etc. The change of any nominal ζ-potential to 0 mV may also be referred to as a neutralization of the ζ-potential. An inversion of a nominal ζ-potential indicates a change in the charge, for example a nominal ζ-potential of plus 10 mV may be inverted to minus 10 mV.

The type of modification (e.g. increase, decrease, reversion, neutralization) of the ζ-potential of mineral micro-particles by equilibrating said micro-particles with a polyphosphate solution, such as a solution of an organic polyphosphate, as taught herein depends on the type of mineral micro-particle and the initial charge and/or ζ-potential thereof. For example, substituting hydroxides for polyphosphates at the surface of positively charged aluminum hydroxide may lead to an inversion of ζ-potential of the aluminum hydroxide micro-particles, while substituting phosphates for organic polyphosphates at the surface of negatively charged aluminum phosphate or calcium phosphate may lead to an increase of the absolute value of the ζ-potential of the aluminum phosphate micro-particles or calcium phosphate micro-particles, respectively.

In particular embodiments, said mineral micro-particle starting material have (i) a zeta-potential of at least −20 and at most −30 mV for aluminum phosphate, when measured at pH 7.0 in distilled water.

(ii) a zeta-potential of at least +10 and at most +20 mV for aluminum hydroxide, when measured at pH 7.0 in distilled water.

(iii) a zeta-potential of at least −10 and at most −20 mV for calcium phosphate, when measured at pH 7.0 in distilled water.

In particular embodiments, the equilibration of aluminum phosphate and/or calcium phosphate micro-particles with a solution of an organic polyphosphate as taught herein, increases the strength of the electrostatic potential and/or the absolute value of the ζ-potential of said micro-particles. Preferably said ζ-potential is increased to at least −20 mV, at least −25 mV, at least −30 mV, at least −35 mV, at least −40 mV, at least −50 mV, at least −60 mV, at least −70 mV, at least −80 mV or at least −90 mV when measured in distilled water, preferably at least −40 mV, at least −50 mV, at least −60 mV or at least −70 mV, more preferably at least −50 mV.

In particular embodiments, the equilibration of aluminum hydroxide micro-particles with a solution of an organic polyphosphate as taught herein cancels or reverts the nominal electrostatic potential of said micro-particles and/or the nominal ζ-potential of said micro-particles.

In particular embodiments, the equilibration of the mineral micro-particles as taught herein leads to a decrease in size of said micro-particles. The obtained size of the organically-derivatized mineral micro-particles is typically dependent on the initial size of the starting material mineral micro-particle and on the duration of the equilibration period.

In particular embodiments, said starting material mineral micro-particles have a nominal size of at least 0.1 μm and at most 5 μm when measured in colloidal suspension by Dynamic Light Scattering (DLS) or laser diffraction.

In particular embodiments, the methods as taught herein may afford organically-derivatized mineral micro-particles having a size of at most 1 μm, at most 0.5 μm, at most 0.2 μm or at most 0.1 μm μm, at most 0.05 μm, at most 0.02 μm, preferably at most 0.2 μm. For example, the equilibration procedure as taught herein of aluminum phosphate micro-particles for a period of up to 40 hours may lead to a decrease of a nominal size value of 2 μm for the starting material particles to a nominal size of 0.2 μm for the resulting, organically-derivatized mineral micro-particles. The organically-derivatized micro-particles as taught herein may occur as amorphous aggregates of smaller crystallites or smaller amorphous aggregates of the same crystallite size.

In other particular embodiments, the methods as taught herein may afford organically-derivatized mineral micro-particles having a size which is smaller than the starting material particles, for instance, at least about 10% smaller, or at least about 20% smaller, or at least about 30% smaller, or at least about 40% smaller, or at least about 50% smaller, or at least about 60% smaller, or at least about 70% smaller, or at least about 80% smaller, or at least about 90% smaller, relative to the size of the starting material particles, ie. the starting material mineral micro-particles with which a comparison is being made.

The term "equilibration", "equilibrate" or "equilibrating" as used herein refers to act of bringing mineral micro-particles such as aluminum phosphate, amorphous aluminium hydroxyphosphate, aluminum hydroxide and/or calcium phosphate micro-particles into contact with a solution of one or more organic polyphosphates for a certain period of time at a certain temperature, and allowing the flow of matter and/or energy between the mineral micro-particles and the surrounding solution of one or more organic polyphosphates until the micro-particles have no further tendency to undergo further change with time (e.g. no change in ζ-potential). It is assumed that during this period of time a substitution reaction, or ligand exchange, of hydroxide or orthophosphate groups by organic polyphosphate ions takes place at the surface of said mineral micro-particles. This substitution reaction, or ligand exchange continues until an equilibrium is reached.

The step of equilibrating typically comprises mixing of the mineral micro-particles with the solution of one or more organic polyphosphates. Non-limiting examples of devices which can be used to perform the mixing are rocking platforms, rotary carousel, vortexers, mixers (e.g. screw, ribbon or paddle) or blenders (e.g. screw, ribbon, paddle). Furthermore, the mineral micro-particles may be washed before being added to the solution of one or more organic polyphosphates. Preferably, the wash is performed in deionized water. The duration of the equilibration period is dependent on the type of mineral micro-particle (e.g. aluminum phosphate, amorphous aluminium hydroxyphosphate, aluminum hydroxide, and/or calcium phosphate) and/or the purpose of the equilibration (e.g. modifying the size, the electrostatic potential and/or the ζ-potential of said micro-particle) and can vary from at least 1 minute to at least 50 hours. Typically, the modification of the electrostatic potential and/or the ζ-potential of mineral micro-particles as taught herein require a shorter equilibration period compared to the modification of the size. Preferably, the equilibration period for modifying the electrostatic potential and/or the ζ-potential of mineral micro-particles is at most one hour, while the equilibration period for modifying the size of mineral micro-particles is at least one hour. More preferably, the equilibration period for modifying the electrostatic potential and/or the ζ-potential of mineral micro-particles is at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, even more preferably for at least 10 minutes and the equilibration period for modifying the size of mineral micro-particles is at least 5 hours, at least 10 hours, at least 15 hours, at least 20 hours, at least 25 hours, at least 30 hours, at least 35 hours, at least 40 hours, at least 45 hours, at least 50 hours, even more preferably at least 40 hours. In particular embodiments, said equilibration period is performed at room temperature. Optionally, either the solution of one or more organic polyphosphates can be removed from the obtained organically-derivatized mineral micro-particles or the obtained organically-derivatized mineral micro-particles from the solution of one or more organic polyphosphates after the equilibration period. Non-limiting examples of methods to achieve this separation are filtration, centrifugation, optically induced dielectrophoretic (ODEP) forces, buffer exchange, washing, or other techniques known by the skilled person.

In a second aspect the present invention provides organically-derivatized mineral micro-particles which are obtainable by the equilibration method according to the first aspect.

The micro-particles as obtained by the method of the present invention are difficult to describe in exact, objective terms due to the chemical reactions, surface changes and size reduction described above. The measured zeta-potential is changed considerably during the ligand exchange/substitution reaction and must be deemed a consequence of said chemical reactions, surface changes and size reduction. However, experience shows that organically-derivatized mineral micro-particles are repeatedly obtained with substantially identical performance/zeta-potential by following the procedure described. The organically-derivatized mineral micro-particles are thus most precisely described as the product of said equilibration method.

As mentioned above it is assumed that organic polyphosphates react with the surface of aluminium phosphate, or calcium phosphate by ligand exchange with hydroxide ions bound to the metal cation by ionic bonds. Measurement of changes in zeta-potential of the particles is a direct evidence of the adsorption of ions at the interface between the particle physical surface and the bulk solvent (the so-called Helmholtz plane). In the case of negatively charged, organic polyphosphates adsorption to negatively charged surface is not favorable due to electrostatic repulsion. However, the experimental data presented herein shows that the zeta-potential of aluminium phosphate is increased upon treatment by organic polyphosphates, showing specific adsorption of organic polyphosphates to aluminium phosphate particles. In addition, the data shows that the increased zeta potential values of aluminium phosphate particles treated with organic polyphosphates (compared to non-treated particles or ortho-phosphate treated particles) are conserved after extensive washing of the particles with de-ionized water. The data indicates that organic polyphosphates are strongly bound to the particle surface, providing supporting evidence that ligand exchange has occurred.

Therefore, monitoring the change in zeta-potential of particles as a function of time gives the kinetics of adsorption of organic polyphosphates at the surface of particles (Helmholtz plane). However, this method does not give the kinetics of ligand exchange for hydroxide ions. Ligand exchange rates for Al (III) are some of the slowest recorded in aluminium (III) hydrates (Martin R. B., The chemistry of aluminum as related to biology and medicine. Clinical Chemistry, 1986, 32:1797-806). However, in the case of aluminium phosphate, where Al (III) is mostly complexed with phosphate, the kinetics of ligand exchange for hydroxide in Al (III) are unknown.

Direct evidence for ligand exchange, using spectroscopy, is expected to be less challenging than for the analogous reaction using inorganic polyphosphates because of the presence of carbon in these molecules and the presence of phospho-ester bonds, which will give a distinct signature in analytical spectroscopy such as Raman or IR, a chemical signature not initially present in the original un-modified particles. Inorganic polyphosphates consisting of polymers of phosphoric acid show the characteristic features of orthophosphate already present in aluminium phosphate or calcium phosphate particles. The Raman spectrum of the particle surface modified with organic polyphosphates is expected to be different than that of the initial un-modified particles. Moreover, hydroxide ions released from the ligand exchange reaction will lead to alkalization of the solution, and pH measurements as a function of time may therefore also reveal the kinetics of ligand exchange.

In particular embodiments, the method as taught herein starts from commercially available (unmodified) aluminum phosphate, amorphous aluminium hydroxyphosphate, aluminum hydroxide, and/or calcium phosphate micro-particles which are subsequently modified. Preferably, said starting material aluminum phosphate micro-particles are ADJU-PHOS® micro-particles and said unmodified (i.e. starting material) aluminum hydroxide micro-particles are ALHYDROGEL® micro-particles, more preferably ADJU-PHOS® 2% or ALHYDROGEL® 2% micro-particles, respectively. Preferably, said starting material calcium phosphate micro-particles are non-hydroxyapatite micro-particles. In further particular embodiments, the aluminum phosphate or calcium phosphate micro-particles may comprise a portion of hydroxyl groups. In even further particular embodiments, the aluminum phosphate or calcium phosphate micro-particles may comprise small fractions of other chemical compounds or elements, such as sodium chloride (e.g. 0.8%-1.0% w/w), chloride (e.g. ≤0.33% w/w) nitrogen (e.g. ≤0.05% w/w), nitrate (e.g. ≤100 ppm), sulphate (e.g. ≤0.1% w/w), iron (e.g. ≤15 ppm), arsenic (e.g. ≤1 ppm), heavy metals (e.g. ≤20 ppm), ammonium (e.g. ≤50 ppm).

In particular embodiments, the methods comprising a step of equilibrating said aluminum hydroxide, aluminum phosphate, amorphous aluminium hydroxyphosphate and/or calcium phosphate micro-particles with said solution of one or more organic polyphosphates as taught herein leads to a partial or complete substitution of the hydroxide ions or phosphate ions which are located at the surface of the micro-particle by organic polyphosphate ions.

The term "substitution" as used herein refers to the replacement of an anion by another in a solid matrix, also called ligand-exchange. Due to their opposite charge, cations and anions will be attracted to each other because of the Coulomb forces they may mutually exert onto each other. As the interatomic distance decreases, it will become short enough that the electron from the valency shell of the anion will move to the valency shell of the cation thereby forming an ionic bond (electrovalent). For comparison, in aluminum hydroxide, aluminum ($Al^{3+}$) is engaged in an ionic bond with hydroxide (OH. Ionic bonds as opposed to covalent bonds are not localized. The maximal surface coverage of aluminum phosphate, aluminum hydroxide or calcium phosphate micro-particles by organic poly-phosphate ions may be in the range of 0.2% to 0.8% (w: w), in the assumption that the micro-particles have a simple spherical shape and a monolayer coverage of the surface by organic polyphosphate ions.

The term "surface" as used herein refers to the outer boundary of a three-dimensional structure, such as a micro-particle, protein, peptide, polypeptide, biomolecule or antigen, which is accessible for interaction with solvents (e.g. water) and solutes, (e.g. ions) from the surrounding liquid medium (e.g. liquid buffer), also called the solvent-accessible surface. The solvent-accessible surface of the mineral micro-particles as taught herein may be determined or extrapolated from binding isotherms.

In particular embodiments, the equilibration of said mineral micro-particles with a solution of one or more organic polyphosphates as taught herein increases the biomolecule-binding and/or biomolecule adsorption capacities of said mineral micro-particles. The biomolecule-binding and/or biomolecule adsorption capacity of said organically-derivatized mineral micro-particles selected from the list consisting of aluminum phosphate, amorphous aluminium hydroxyphosphate, aluminum hydroxide and/or calcium phosphate micro-particles can be at least 1.5-fold, at least 2-fold, at least 2.5-fold, at least 3-fold, at least 3.5-fold, at least 4-fold, at least 5-fold, at least 5.5-fold, at least 6-fold higher than the biomolecule-binding and/or biomolecule adsorption properties of starting materials selected from aluminum phosphate, aluminum hydroxide or calcium phosphate micro-particles. Preferably, said biomolecules are antigens.

The term "bind", "interact", "specifically bind" or "specifically interact" as used throughout this specification means that an agent binds to or influences one or more desired molecules or analytes substantially to the exclusion of other molecules which are random or unrelated, and optionally substantially to the exclusion of other molecules that are structurally related. The term "bind", "interact", "specifically bind" or "specifically interact" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold greater, than its affinity for a non-target molecule.

The binding or interaction between the agent and its intended target(s) may be non-covalent (i.e., mediated by non-covalent forces, such as for example, ionic interactions, hydrogen bridges, dipolar interactions, van der Waals interactions, and the like). Preferably, the agent may bind to or interact with its intended target(s) with affinity or association constant (KA) of such binding $K_A \geq 1\times10^6\ M^{-1}$, more preferably $K_A \geq 1\times10^7\ M^{-1}$, yet more preferably $K_A \geq 1\times10^8\ M^{-1}$, even more preferably $K_A \geq 1\times10^9\ M^{-1}$, and still more preferably $K_A \geq 1\times10^{10}\ M^{-1}$ or $K_A \geq 1\times10^{11}\ M^{-1}$, wherein $K_A$=[A_T]/[A][T]=ka/ka, A denotes the agent, T denotes the intended target, ka denotes the rate of adsorption and ka denotes the rate of desorption. Determination of $K_A$ can be carried out by methods known in the art, such as for example, using equilibrium dialysis and Scatchard plot analysis.

To increase the strength of the electrostatic potential responsible for the attraction of biomolecules (and binding strength) to the surface of the micro-particles, the absolute value of the ζ-potential of the modified micro-particles is preferably as high as possible. Furthermore, as a higher surface/mass ratio leads to higher potential loads of biomolecule per unit of mass of adjuvant, the size of the modified micro-particles is in the sub-micron range, preferably in the nanometer range. Preferably, said biomolecule is a vaccine antigen.

A first general mechanism by which soluble ionic species may adsorb to the surface of particles is through attractive long-range electrostatic forces. These forces are recognized as the most critical determinant in the adsorption of biomolecules, such as antigens, to the surface of micro-particles (e.g. adjuvant micro-particles). Following this mechanism, it would result that biomolecules, such as antigens, get trapped in the attractive electrostatic field of the micro-particle, the aforementioned diffuse layer, with the freedom to diffuse within the diffuse layer and in-and-out to the bulk solvent. As the biomolecules approach the surface of the particle, other short-range forces might be taking place, such as Van der Waals forces, or dipole-dipole interactions (hydrogen-bonds). Solvent effects (hydrophobic effect) might also add to the mechanisms and the total binding strength of the biomolecule to the surface of the particle.

The inventors found that by increasing the nominal negative electrostatic potential of aluminum phosphate micro-particles by equilibrating said micro-particles in a solution of one or more organic polyphosphates, such as a solution of a single organic polyphosphate as taught herein, the strength of this electrostatic field was increased as well, which in turn increased the binding capacity of biomolecules, such as antigen proteins, of opposite (positive) charge. Furthermore, without wishing to be bound by any theory, the present inventors hypothesize that substituting hydroxides for organic polyphosphates at the surface of positively charged aluminum hydroxide may lead to an inversion of ζ-potential, allowing for adsorption of positively charged biomolecules, such as antigen proteins, which are normally electrostatically repelled from aluminum hydroxide micro-particles.

Without wishing to be bound by any theory, the present inventors hypothesize that a second mechanism by which biomolecules, such as antigens, may bind to the surface of mineral micro-particles as taught herein is through more specific interactions involving the formation of ionic bonds between the positively charged amino acids at the protein surface of a biomolecule, preferably lysine and arginine, and the negatively charged organic phosphate groups at the surface of the micro-particles (e.g. adjuvant micro-particles). The affinity of phosphate groups for positively charged amino acids residues in proteins, especially lysine and arginine, is well documented in biochemistry, with the example of protein kinases and phosphatases where the phosphoryl group of nucleotides is transiently involved in ionic pairing with lysine or arginine residues of the enzyme catalytic site (Mavri J, and Vogel M. J., Ion pair formation of phosphorylated amino acids and lysine and arginine side chains: A theoretical study, Proteins Structure Function and Bioinformatics, 1996). In some particular cases of protein-protein interactions, it has been shown that this type of ionic bond can be as strong as a covalent bond (Woods A. S, and Ferre S., Amazing stability of the arginine-phosphate electrostatic interaction, Journal of Proteome Research, 2005), and this property is being exploited in some applications (Fokkens M. et al., A molecular tweezer for lysine and arginine, Journal of the American Chemical Society, 2005; Schug K. A. et al., Noncovalent binding between guanidinium and anionic groups: focus on biological-and synthetic-based arginine/guanidinium interactions with phosph [on]ate and sulf [on]ate residues, Chemical Reviews, 2005). The present inventors further hypothesize that this type of interaction can occur at the surface of phosphate containing micro-particles (e.g. used as adjuvants) such as aluminum- or calcium-phosphates, at appropriate pH values and ionic strength of the bulk solvent. Furthermore, the introduction of organic polyphosphate ions at the surface of mineral micro-particles as taught herein may improve this binding mechanism in the way that, due to their polymeric nature and conformational flexibility, organic polyphosphates may chelate positively charged amino acids residues, preferably Lysine or Arginine side chains. As a result, the binding capacity or binding strength for biomolecules, such as antigens, presenting such basic residues at their surface may be dramatically improved due to chelate effects. Interestingly, in the comparative case of aluminum hydroxide, which is positively charged, the substitution of some hydroxide ions by organic polyphosphate ions may create some sites for the specific adsorption of positively charged biomolecules, such as antigens, which are otherwise expected to show poor affinity for aluminum hydroxide due to repulsive charge-charge interactions, at pH values commonly used for applications of biomolecule delivery or adsorption systems, such as vaccine production.

Another aspect of the invention relates to organically-derivatized mineral micro-particles selected from the list consisting of aluminum phosphate, amorphous aluminium hydroxyphosphate, aluminum hydroxide and/or calcium phosphate micro-particles, wherein the orthophosphate ions located at the surface of the aluminum phosphate or calcium phosphate micro-particles or the hydroxide ions located at the surface of the aluminum hydroxide micro-particles are partly or completely substituted by organic polyphosphate ions.

In particular embodiments, the organically-derivatized mineral micro-particles as taught herein have (i) a nominal ζ-potential of at least −40 mV, for aluminum phosphate, when measured at pH 7.0 in distilled water, or (ii) a nominal ζ-potential of at least −20 mV, for aluminum hydroxide, when measured at pH 7.0 in distilled water, or (iii) a nominal ζ-potential of at least −40 mV, for calcium phosphate, when measured at pH 7.0 in distilled water.

In particular embodiments, the modified aluminum phosphate micro-particles have a nominal ζ-potential of at least −20 mV, at least −25 mV, at least −30 mV, at least −35 mV, at least −40 mV, at least −50 mV, at least −60 mV, at least −70 mV, at least −80 mV or at least −90 mV when measured in distilled water, preferably at least −40 mV, at least −50 mV, at least −60 mV, at least −70 mV, more preferably at least −50 mV.

In particular embodiments, the organically-derivatized mineral micro-particles selected from the list consisting of aluminum phosphate, amorphous aluminium hydroxyphosphate, aluminum hydroxide and/or calcium phosphate micro-particles according to the invention have a nominal size of at least 0.01 μm, and at most 2 μm, at most 1 μm, at most 0.5 μm, at most 0.2 μm, at most 0.1 μm, at most 0.05 μm, at most 0.02 μm, preferably at most 2 μm.

In particular embodiments, the organically-derivatized aluminum phosphate according to the invention have a stoichiometric ratio of Al to P of 1.2+/−0.15 to 1.

In particular embodiments, the organically-derivatized calcium phosphate according to the invention have a stoichiometric ratio of Ca to P of 1.7+/−0.20 to 1.

In particular embodiments, the organically-derivatized mineral micro-particles as taught herein may have a maximal surface coverage of said micro-particles by organic polyphosphate ions of 0.2 to 0.8% W: W.

As noted above, mineral-containing adjuvants, including aluminum phosphate, aluminum hydroxide and calcium phosphate, have been used successfully in vaccine preparation for decades to enhance the immune response against killed, inactivated and subunit antigens.

In particular embodiments, the organically-derivatized mineral micro-particles as taught herein have increased biomolecule-binding properties compared to starting material aluminum hydroxide, aluminum phosphate, amorphous aluminium hydroxyphosphate and/or calcium phosphate micro-particles, preferably wherein said biomolecule has an opposite charge than said modified micro-particle or wherein said biomolecule is neutral when said modified micro-particle is neutral. For example, organically-derivatized aluminum phosphate micro-particles are negatively charged and preferably bind to positively charged biomolecules.

The term "biomolecules" as used herein is meant to include ingredients or agents that are derived from living organisms by purification or by synthesis and which may be biologically active. Also covered by these terms are diagnostic agents as well as so-called "cosmeceuticals". Diagnostic agents include, for example, fluorescent proteins (e.g. green fluorescent protein or GFP) or radiolabeled molecules. Cosmeceuticals include active ingredients that have an effect on the outer appearance of an individual such as on skin, hair, lips, and eyes, and encompass anti-wrinkling agents and agents that improve complexion. In these applications the modified micro-particles as taught herein preferably are administered externally. Active pharmaceutical ingredients (also referred to as medicinal products or drugs) are of particular interest and form a subgroup of biomolecules.

The biomolecules may include small molecules (such as those having a molecular weight of less than about 1,500), synthetic or natural such as monosaccharides, disaccharides, trisaccharides, oligosaccharides, peptides, nucleic acids but also nucleic acid analogues and derivatives; or large molecules, including plasmids, vectors, polysaccharides, biological macromolecules, e.g., larger peptides (polypeptides), proteins, peptide analogues and derivatives thereof, peptidomimetics, nucleic acid based molecules (e.g. DNA, RNA, mRNA, tRNA, RNAi, SIRNA, microRNA, or any other DNA or RNA-like molecules), polynucleotides, oligonucleotides, enzymes, antibiotics, extracts made from biological materials such as bacteria, plants, fungi, or animal cells or tissues, therapeutic agents, preventatives, diagnostic agents, imaging agents, aptamers (including oligonucleotide or protein aptamers).

In one embodiment the biomolecules are water-soluble, particularly are water-soluble active pharmaceutical ingredients. Such ingredients may belong to Class I or III of the Biopharmaceutical Classification System (BCS), which classifies drug substances into four classes: Class I-High Permeability, High Solubility; Class II-High Permeability, Low Solubility; Class III-Low Permeability, High Solubility; Class IV-Low Permeability, Low Solubility. Water-soluble drugs can also be specified by the amount of a water (g) required to solve 1 g of a compound, wherein water-soluble drugs are those fulfilling the following solubility qualifications: 10-30 g ("soluble"); 30-100 g ("sparingly soluble"); 100-1000 g ("slightly soluble"); 1000-10000 g ("very slightly soluble" or "poorly soluble"); or particularly soluble, sparingly soluble and slightly soluble drugs.

In another embodiment, the biomolecules may be antibodies or antibody fragments. The term "antibody" is meant to include monoclonal antibodies, polyclonal antibodies and multispecific antibodies (e.g. bispecific antibodies). Antibody fragments comprise a portion of an antibody, generally the antigen binding or variable region thereof. Examples of antibody fragments include Fab, Fab', $F(ab')_2$ and Fv fragments; diabodies; linear antibodies; single-chain antibody molecules; multispecific antibodies formed from antibody fragments.

In preferred embodiments, the biomolecules may be antigens which are capable of inducing an immune response in a host organism. Accordingly, in preferred embodiments, the organically-derivatized mineral micro-particles as taught herein have increased antigen-binding properties compared to starting material aluminum phosphate, amorphous aluminium hydroxyphosphate, aluminum hydroxide and/or calcium phosphate micro-particles, preferably wherein said antigen has an opposite charge than said modified micro-particle or wherein said antigen is neutral when said modified micro-particle is neutral. For example, modified aluminum phosphate micro-particles are negatively charged and preferably bind to positively charged antigens.

The term "host organism" typically denotes animals, preferably vertebrates, including birds, humans and non-human mammals, such as mice, rats, hamsters, guinea pigs, pigs, cows, horses, sheep, goats, dogs, cats or primates.

In particular embodiments, the organically-derivatized mineral micro-particles as taught herein may have increased antigen adsorption capacities as a result of their increased antigen-binding capacities. These increased antigen adsorption capacities will make it possible to make combination vaccines that may contain antigens from a higher number of infectious agents compared to what is available in the prior art. The protein adsorption capacities of an adjuvant can be measured using a variety of analytical methods. For example, by comparing the protein content in the aqueous phase of the antigen solution before and after adsorption onto the adjuvant (Lindblad E., Aluminum compounds for use in vaccines, Immunology and Cell Biology, 2004,82: 497-505), or in case that an antibody specific for the desired antigen is available, adsorption, the protein adsorption capacities can be measured using immunoprecipitation techniques, by using either quantitative immunoelectrophoresis or single radial immunodiffusion. Without the use of an antibody it can be tested by spectrophotometrically (Lindblad E., Aluminum compounds for use in vaccines, Immunology and Cell Biology, 2004,82:497-505).

The term "adsorption" as used herein refers to physisorption (e.g. by van der Walls force) or chemisorption (e.g. by covalent or ionic bond) wherein the bond between the surface of the micro-particles and the biomolecule (e.g. antigen and/or organic molecule) is established.

In particular embodiments, the biomolecule-binding properties of said organically-derivatized mineral micro-particles selected from the list consisting of aluminum hydroxide, aluminum phosphate, amorphous aluminium hydroxyphosphate and/or calcium phosphate micro-particles are at least 1.5-fold, at least 2-fold, at least 2.5-fold, at least 3-fold, at least 3.5-fold, at least 4-fold, at least 5-fold, at least 5.5-fold, at least 6-fold higher than the biomolecule-binding properties of starting material aluminum hydroxide, aluminum phosphate, amorphous aluminium hydroxyphosphate and/or calcium phosphate micro-particles, preferably wherein said biomolecule is an antigen. The ratio of adsorbed biomolecule (e.g. antigen) over aluminum hydroxide (mg/g), aluminum phosphate (mg/g), amorphous aluminium hydroxyphosphate (mg/g) or calcium phosphate (mg/g) micro-particles depends on the combination of the type of modified micro-particle and the nature of the biomolecule (e.g. antigen). For example, the ratio of biomolecule (e.g. antigen) over mineral micro-particle (mg/g) may be at least 3, at least 4, at least 5, at least 6, at least 7, at least 8, at least 9, at least 10, at least 11, at least 12, preferably at least 12.

The organically-derivatized mineral micro-particles selected from the list consisting of aluminum hydroxide, aluminum phosphate, amorphous aluminium hydroxyphosphate and/or calcium phosphate micro-particles according to the present invention may have improved physico-chemical properties i.e. increased colloidal stability or reduced aggregation, which may be due to increased electrostatic repulsion between particles; and/or improved biomolecule adsorption and binding, preferably wherein said biomolecule is an antigen.

Furthermore, another aspect of the invention is the use of said organically-derivatized mineral micro-particles as taught herein in medicine.

In particular embodiments, "medicine" may be human and/or veterinary medicine.

In particular embodiments, the organically-derivatized mineral micro-particles as taught herein may be used as biomolecules delivery or adsorption systems, preferably wherein said biomolecules delivery system is a vaccine adjuvant.

In particular embodiments, said organically-derivatized mineral micro-particles as taught herein may be used in vaccines, preferably as biomolecules delivery systems, more preferably as vaccine adjuvants.

In particular embodiments, said organically-derivatized mineral micro-particles as taught herein may be used for manufacturing a vaccine.

In other particular embodiments organically-derivatized mineral micro-particles prepared from a starting material selected from aluminum hydroxide, aluminum phosphate, amorphous aluminum hydroxyphosphate and/or calcium phosphate micro-particles may be used for manufacturing a vaccine adjuvant or vaccine component, and/or may be used in the manufacturing of a vaccine.

Modified mineral micro-particles which have antigens bound to their surface as taught herein can be used to raise antibodies, such as polyclonal antibodies, in animals. This is achieved by injection of said mineral micro-particles which have antigens bound to their surface into laboratory or farm animals in order to raise high expression levels of antigen-specific antibodies in the serum, which can then be recovered from the animal. Polyclonal antibodies can be recovered directly from serum, while monoclonal antibodies are produced by fusing antibody-secreting spleen cells from immunized mice with immortal myeloma cell to create monoclonal hybridoma cell lines that express the specific antibody in cell culture supernatant.

Therefore, another aspect of the invention is the use of the organically-derivatized mineral micro-particles according to the invention, for antibody production.

Mineral micro-particles capable of binding biomolecules and/or contaminants (i.e. arsenic, chromium, nitrate, calcium, radium, uranium, fluoride) can be used as biomolecules adsorption systems, for example in processes of purification, separation, and decontamination of aqueous and other ion-containing solutions (e.g. by functioning as ion exchangers). For example, positively charged mineral micro-particles may be capable of binding albumin, which is negatively charged, and can therefore be used for the removal of albumin from blood samples. In another example, charged mineral micro-particles can be used to selectively enrich acidic or basic proteins in a variety of samples. At an industrial scale, purification, separation, and decontamination is often performed using sorption columns (e.g. ion exchange chromatography).

Accordingly, the organically-derivatized mineral micro-particles as taught herein may be used as biomolecules adsorption systems in purification, separation, and decontamination processes.

In particular embodiments, the organically-derivatized mineral micro-particles as taught herein may be used for the removal of undesired proteins during blood fractionation.

The present invention is further illustrated in the following non-limiting examples.

EXAMPLES

Experiment no.1

Adsorption of the model antigen hen-egg lysozyme (HEL) was carried out with ADJU-PHOS® particles treated with inositol-hexaphosphate (IP6) and compared to meta-hexaphosphate (m6Pi), orthophosphate (Pi) and water as controls. ADJU-PHOS® at 20 g/L was treated by addition of IP6 or m6Pi to a final concentration of 5 mM and the pH was re-adjusted to pH 5.0, and the suspension was left 12 hours under gentle agitation to equilibrate and to insure no sedimentation of the particles occurred. ADJU-PHOS® particles were then rinsed extensively with ultra-pure water to remove the excess of ions and autoclaved. The pH of the suspension was adjusted to 7.0 before performing HEL adsorption.

Figure 1:
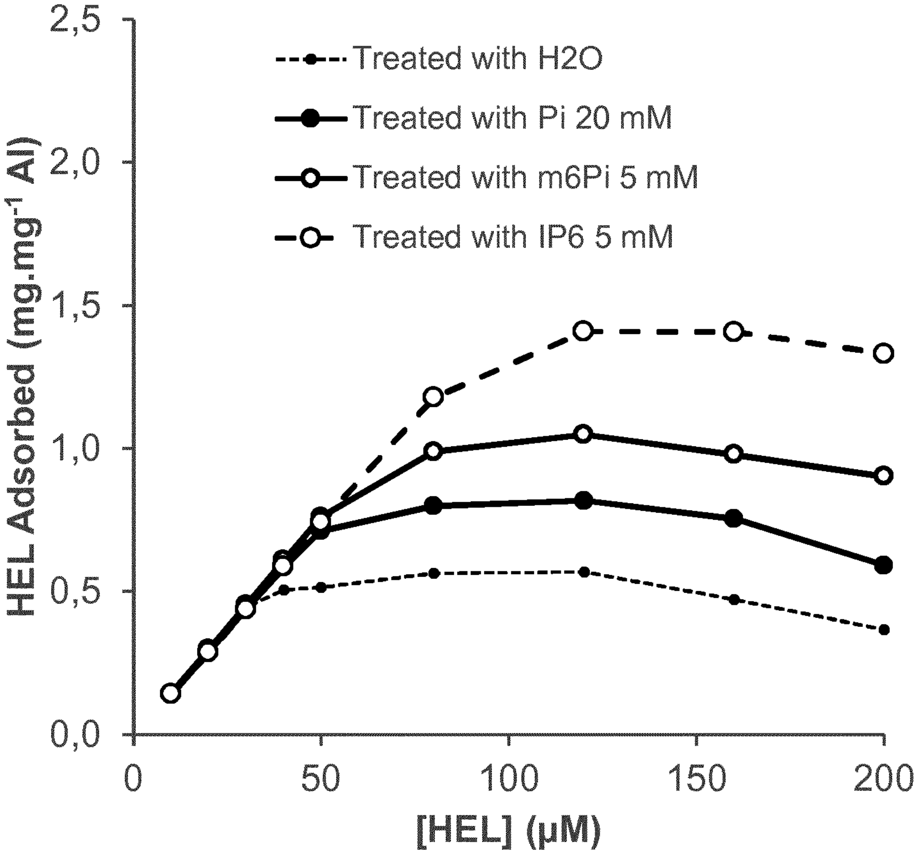
FIG. 1. Adsorption capacity of hen-egg lysozyme (HEL) of ADJU-PHOS® adjuvant particles treated by IP6.

The adsorption capacity of the particles was determined as function of HEL concentration. Serial dilutions from 2 mM stock HEL solution were made and added accordingly to fixed volumes of calcium phosphate particles such as the final concentrations ranged from 10 μM to 120 μM, and the final concentration of calcium phosphate particles was 4 mg/mL. Mixtures were left for equilibration 30 min at room temperature under agitation to insure no sedimentation of the particles occurred. The amounts of adsorbed HEL were determined from the amounts left in the supernatant after sedimentation of the particles. The results are shown in FIG. 1.

Experiment no.2

Figure 2:
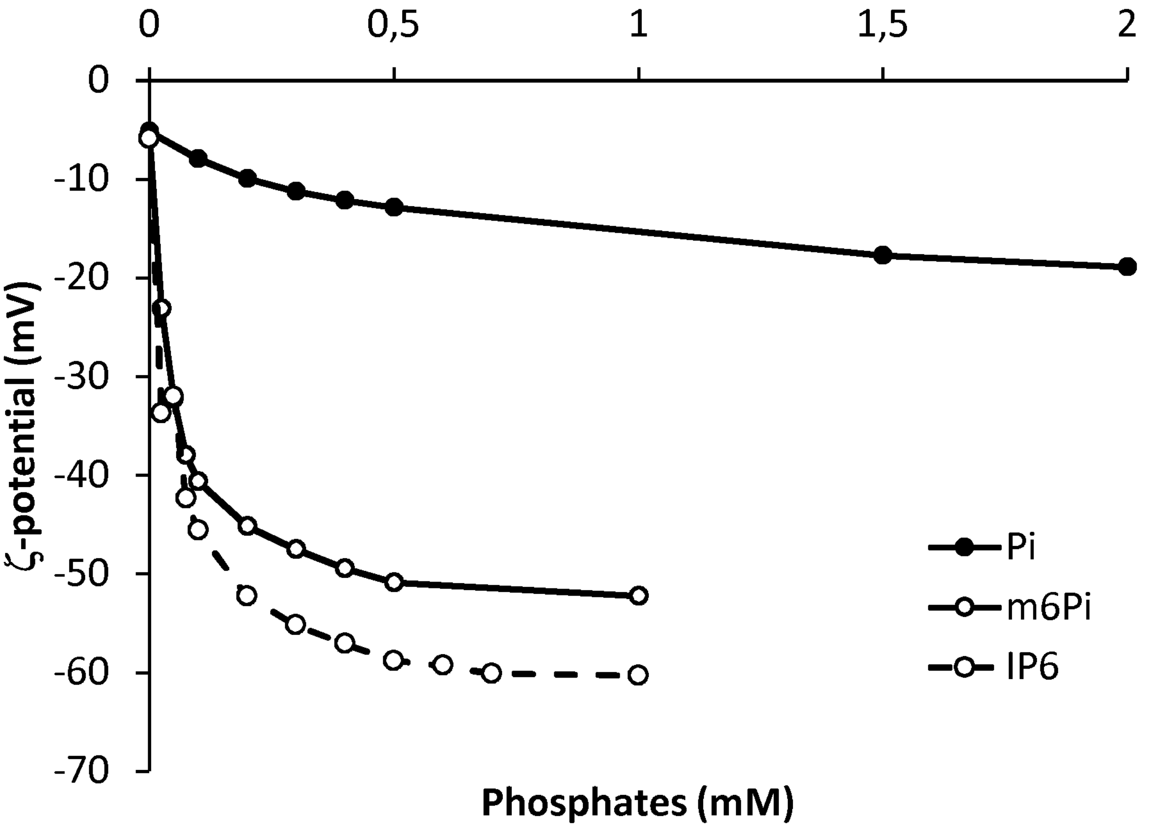
FIG. 2: Effect of inositol hexaphosphate (IP6) on calcium phosphate adjuvant particles zeta-potential.

Effect of inositol-6-phosphate (I6P) concentration on the zeta potential of calcium phosphate particles. Calcium phosphate adjuvant particles (Brenntag-Biosector, Denmark) were rinsed extensively with ultra-pure water (6 uS/cm) before being treated for 60 minutes at room temperature with various concentrations of orthophosphate (Pi), meta-hexaphosphate (m6Pi) or inositol-hexaphosphate (IP6). Zeta potential measurements were performed with a Zetasizer Nano ZS (Malvern, U.K.) on 10× dilutions of the initial suspension of rinsed particles, in the corresponding phosphate solutions. The results are shown in FIG. 2.

Experiment no.3

Figure 3:
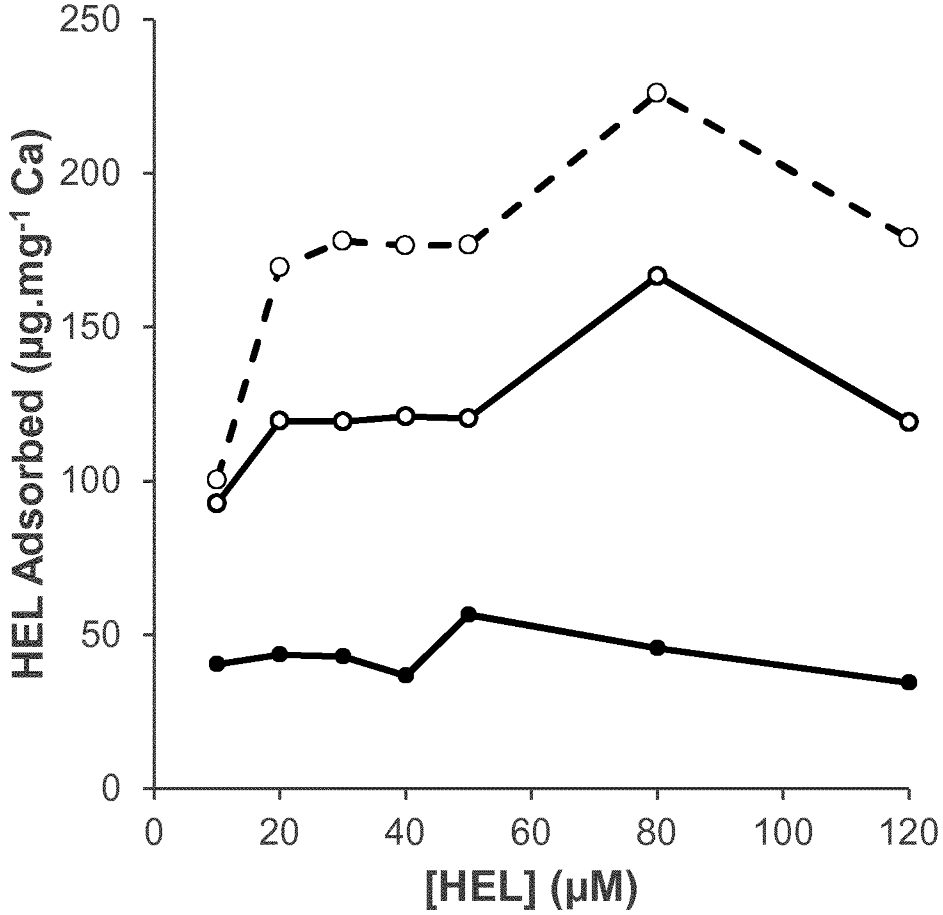
FIG. 3: Adsorption capacity of hen-egg lysozyme of calcium phosphate particles treated with inositol hexaphosphate (IP6).

Adsorption of model antigen hen-egg lysozyme (HEL) was carried out with calcium phosphate particles treated with 0.2 mM phosphates, in order to determine the adsorption capacity of the particles as function of HEL concentration. Serial dilutions from 2 mM stock HEL solution were made and added accordingly to fixed volumes of calcium phosphate particles such as the final concentrations ranged from 10 μM to 120 μM, and the final concentration of calcium phosphate particles was 4 mg/ml. Mixtures were left for equilibration 30 min at room temperature under agitation to insure no sedimentation of the particles occurred. The amounts of adsorbed HEL were determined from the amounts left in the supernatant after sedimentation of the particles. The results are shown in FIG. 3.

Experiment no.4

Figure 4:
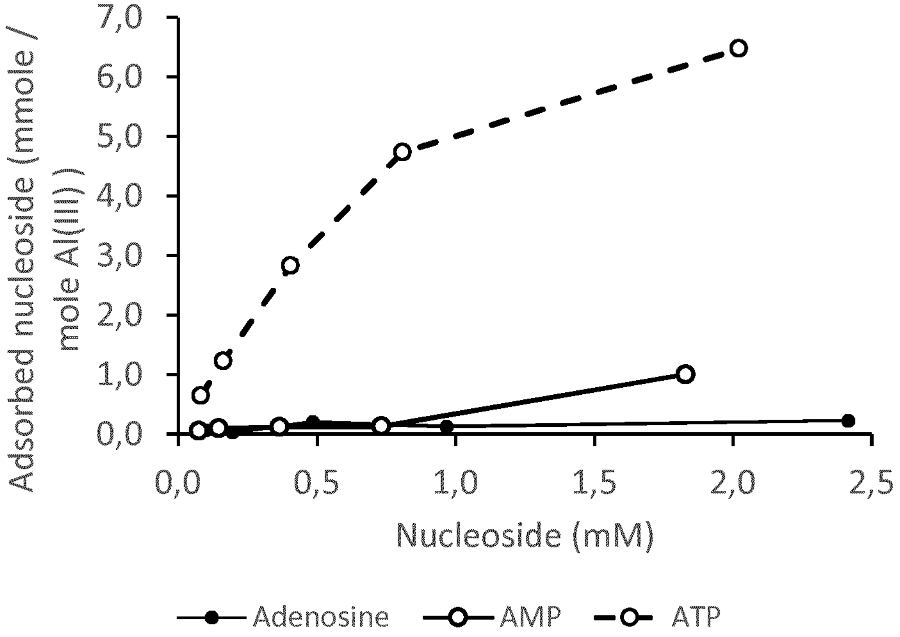
FIG. 4: Adsorption capacity of adenosine, adenosine-5'-monophosphate (AMP) and adenosine-5'-triphosphate (ATP) to ADJU-PHOS® particles.

The degree of phosphorylation of adenosine nucleotides on adsorption to ADJU-PHOS® was investigated by comparing adenosine triphosphate (ATP) to adenosine monophosphate (AMP) and adenosine (A). ADJU-PHOS® at 1% (w/v) was adjusted to pH 7.0 and was blended with solutions of A, AMP and ATP of concentrations ranging from 0.1 mM to 2.5 mM, and left to equilibrate for 1 hour at room temperature under agitation to avoid ADJU-PHOS® sedimentation. Particles were then spun down and Absorbance measurements at 259 nm were taken on the supernatants. The amounts of adsorbed adenosines were calculated from the differences between initial concentrations and final concentrations after adsorption, using a molar extinction coefficient of 15400 cm 1 $M^{-1}$. The results are shown in FIG. 4.

Experiment no.5

Figure 5:
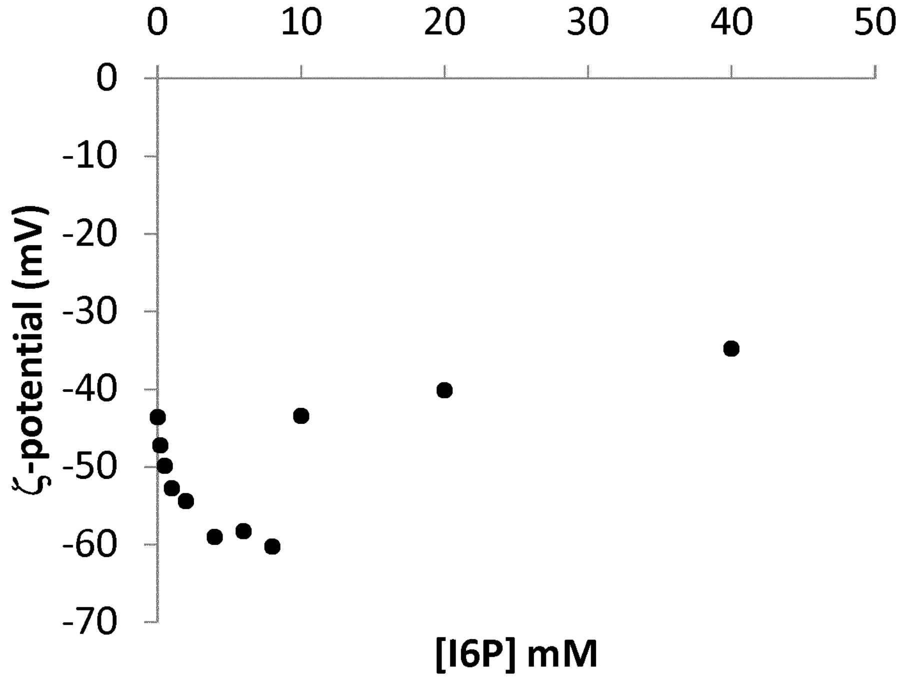
FIG. 5: Effect of inositol hexaphosphate (IP6) concentration on the ζ-potential of Adju-Phos.
Figure 6A:
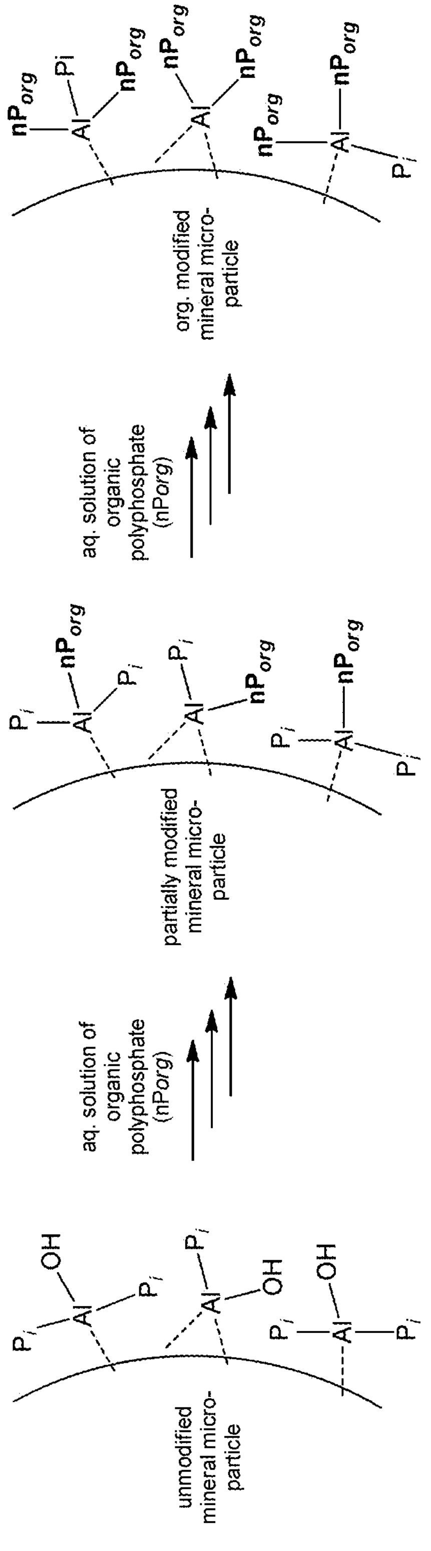
FIGS. 6A and 6B. Hypothetical substitution reaction at the surface of aluminium hydroxyphosphate particles and dissolved organic polyphosphate ions.
Figure 6B:
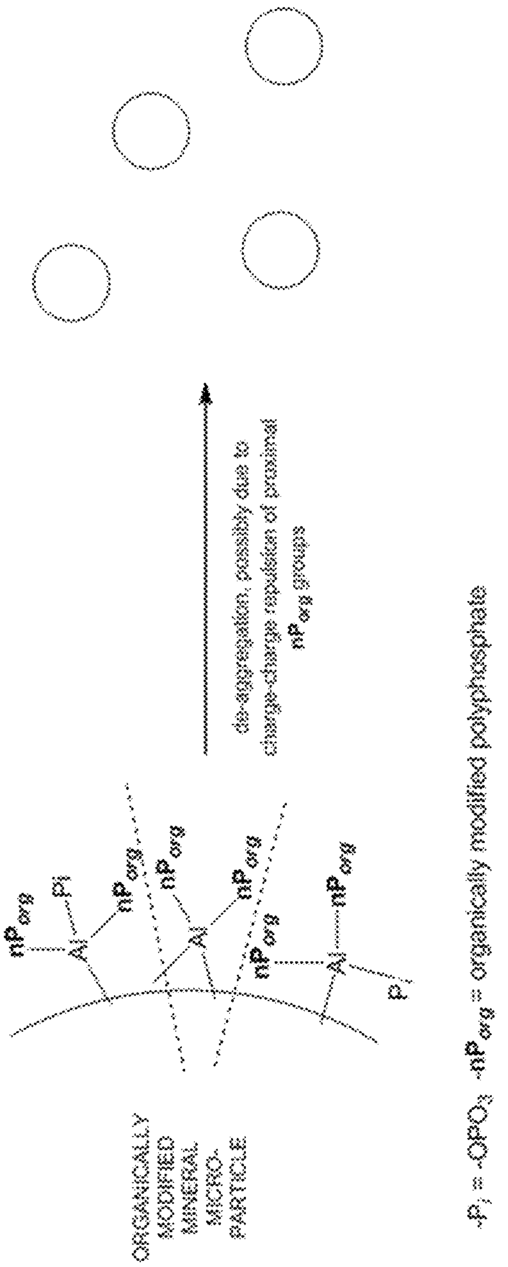
Figure 6C:
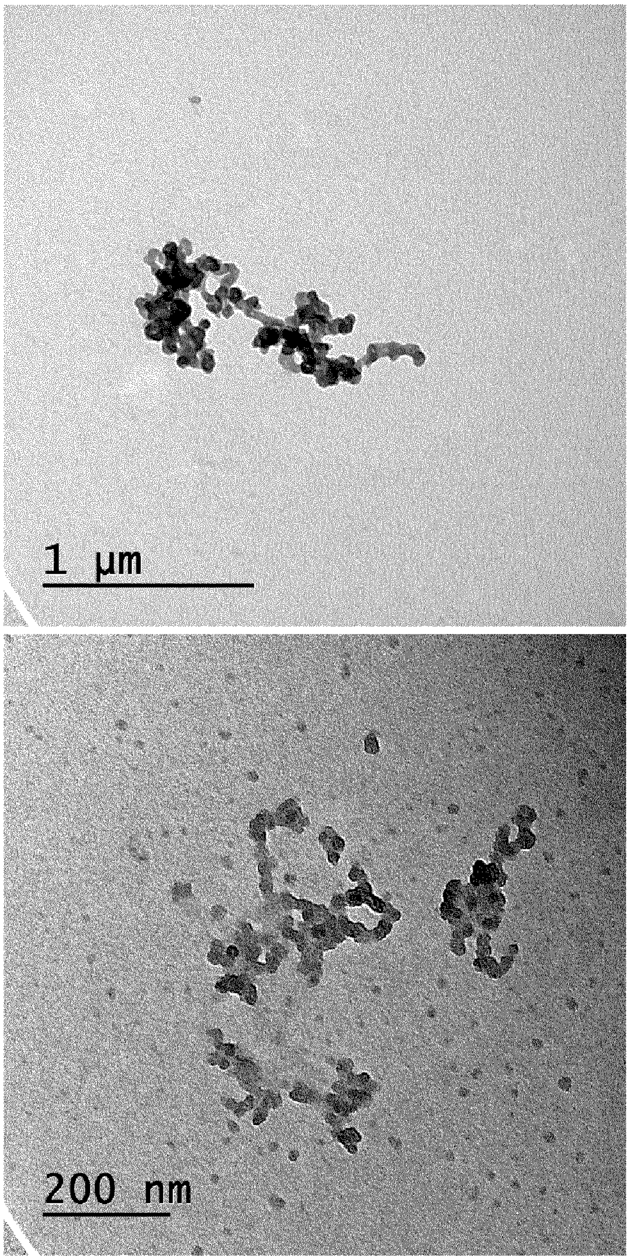
FIG. 6C. Electron micrographs (TEM) of ADJU-PHOS® particles (top) and ADJU-PHOS® ZP (bottom).

The effect of inositol hexaphosphate (IP6) concentration on the zeta-potential of ADJU-PHOS® particles was investigated. ADJU-PHOS® particles were diluted to 0.1% (w: v) in solutions of IP6 of concentrations ranging from 0.2 mM to 40 mM, with pH adjusted to 7.0. After 60 min equilibration at room temperature, ζ-potential was recorded by DLS (Zetasizer Nano ZS, Malvern Instruments). The results are shown in FIG. 5.

Experiment no.6

Figure 7:
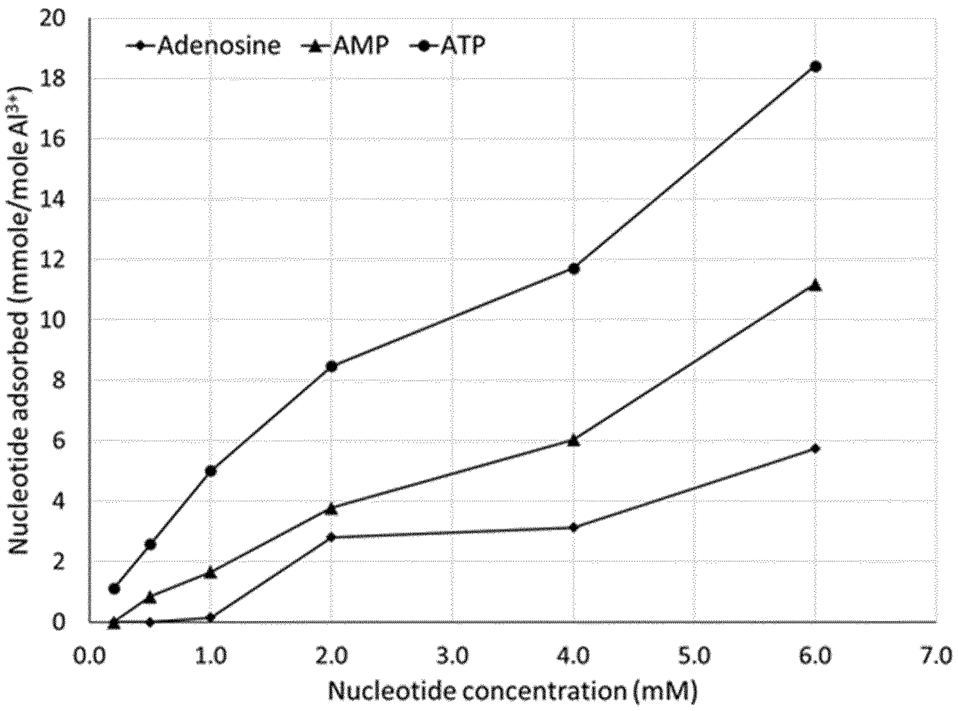
FIG. 7. Adsorption capacity of adenosine, adenosine-5'-monophosphate (AMP) and adenosine-5'-triphosphate (ATP) to ADJU-PHOS® particles.
Figure 8:
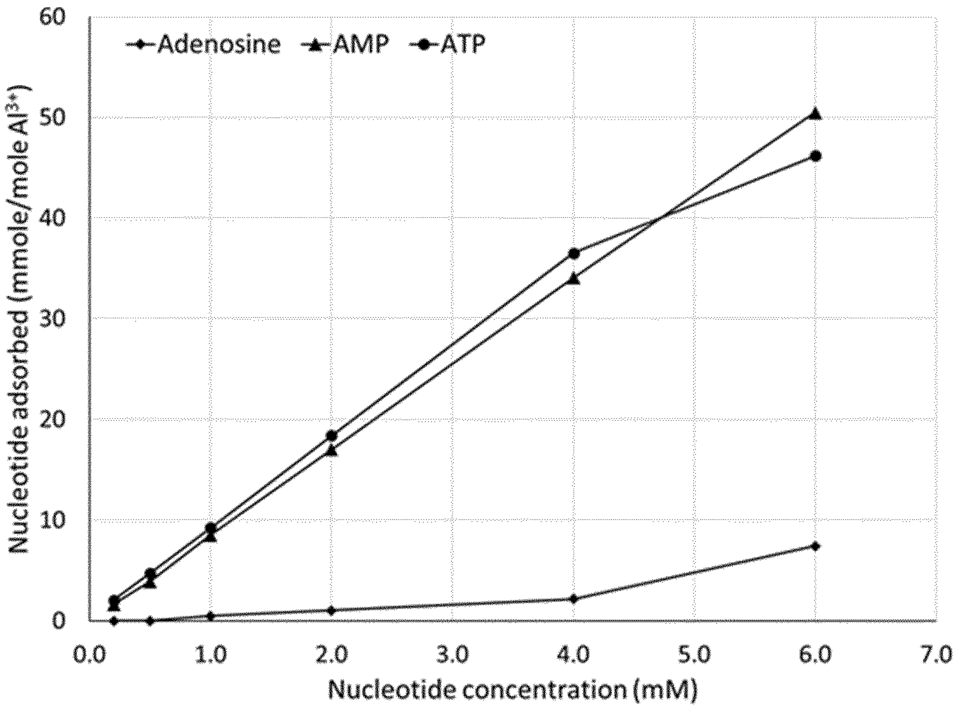
FIG. 8. Adsorption capacity of adenosine, adenosine-5'-monophosphate (AMP) and adenosine-5'-triphosphate (ATP) to ALHYDROGEL® particles.

Adsorption of adenosine nucleotides to ADJU-PHOS® and ALHYDROGEL® was investigated by comparing adenosine triphosphate (ATP) to adenosine monophosphate (AMP) and adenosine (A). ADJU-PHOS® or ALHYDROGEL® at 1% (w/v) were buffered at pH 7.0 with 5 mM imidazole and blended with solutions of A, AMP and ATP of concentrations ranging from 0.2 mM to 6.0 mM and left to equilibrate for 2 hours at room temperature under agitation to avoid adjuvant particles sedimentation. Adjuvant particles were spun down and Absorbance at 259 nm (Absorbance maximum for adenine) was measured on the supernatants with a spectrophotometer. The amounts of adsorbed nucleotides were calculated from the differences between initial concentrations and final concentrations after adsorption, using a molar extinction coefficient of 15400 cm-1 $M^{-1}$ for adenine. The results are shown in FIG. 7 and FIG. 8.

Experiment no.7

Figure 9:
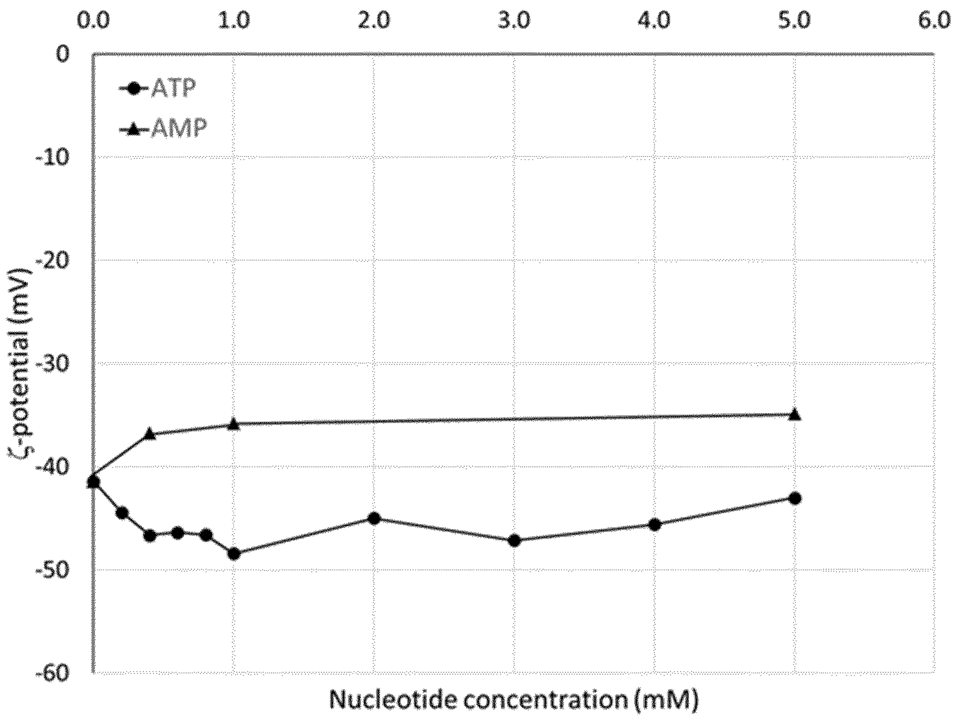
FIG. 9. Effect of adenosine-5'-triphosphate (ATP) and adenosine-5'-monophosphate (AMP) concentration on ADJU-PHOS® ζ-potential.

The effect of adenosine nucleotides (ATP and AMP) on ADJU-PHOS® electrostatic ζ-potential was measured by Dynamic Light Scattering (Zeta-Sizer, Nano series, Malvern). ADJU-PHOS® at 0.2% (w/v) in 5 mM imidazole buffer at pH 7.0 and was blended with solutions of ATP or AMP at concentrations ranging from 0.2 mM to 4.0 mM and left to equilibrate for 2 hours at room temperature under agitation to avoid adjuvant particles sedimentation. Samples were transferred into capillary cells (DTS1060, Malvern) and triplicate measurements were performed at 25° C., after 2 minutes of temperature equilibration. The results are shown in FIG. 9.

Experiment no.8

The effect of adenosine nucleotides (ATP and AMP) on ADJU-PHOS® sedimentation and bed-height was investigated. When ADJU-PHOS® is treated with polyphosphates, in the same conditions of pH and salinity, the packing density of the particulate material increases, leading to a reduced bed-height. A higher packing density of ADJU-PHOS® sediment makes the adjuvant particles more difficult to resuspend into the bulk solvent phase, which can become a burden for vaccine manufacturers. Therefore, monitoring the packing density of modified ADJU-PHOS® is an important parameter for downstream applications.

Figure 10:
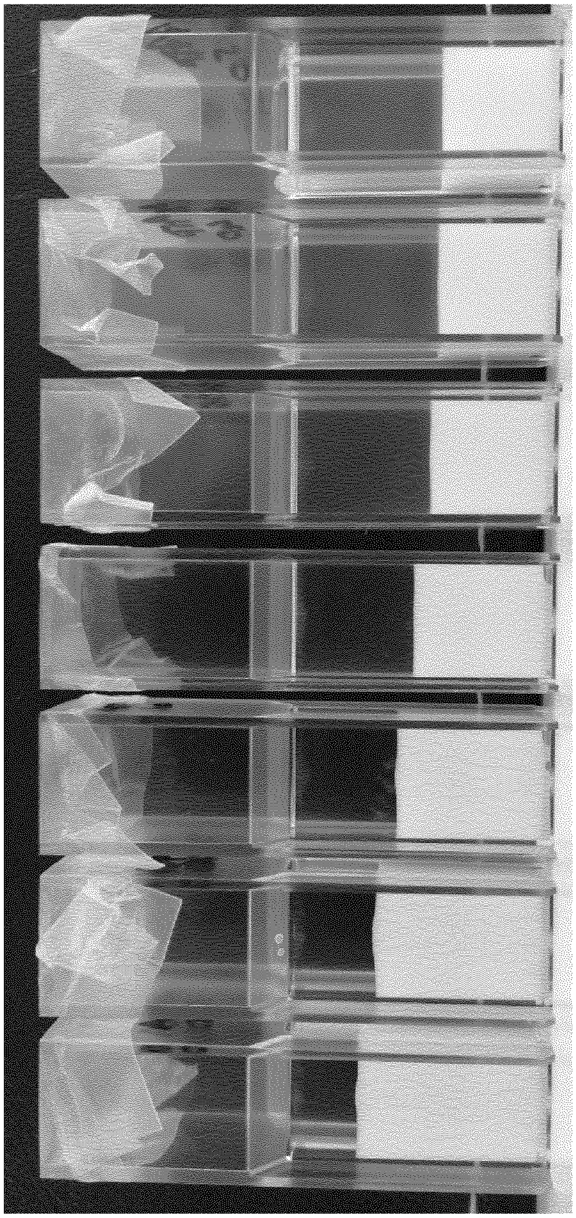
FIG. 10. Effect of adenosine-5'-triphosphate (ATP) and adenosine-5'-monophosphate (AMP) concentration on ADJU-PHOS® sediment bed-height.
Figure 11:
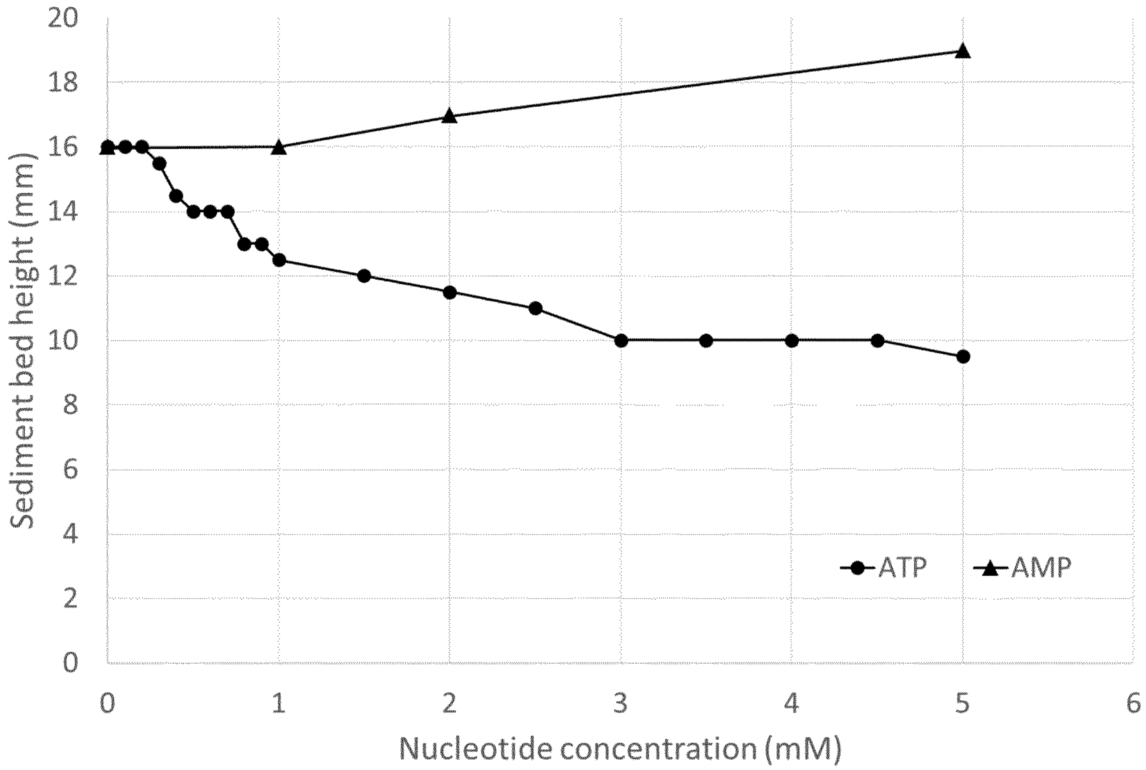
FIG. 11 shows that the bed height of ADJU-PHOS® sediment, measured after 48 hours at rest, decreases as a function of ATP concentration, from 16 mm to 9.5 mm. The most dramatic decrease in bed-height occurs from 0.0 to 1.0 mM ATP, which corresponds to the concentration range where ADJU-PHOS® ζ-potential is the most increased (FIG. 9), suggesting that the two parameters are linked. Interestingly, AMP treatment leads to an opposite effect where ADJU-PHOS® sediment bed-height is increased as a function of the concentration. It appears as if the tri-phosphate chain on adenosine-5'-triphosphate induces a packing of ADJU-PHOS® particles despite the increased-potential, from which electrostatic repulsion forces are expected to keep particles apart from each-other. A similar pattern is observed with inorganic polyphosphates and phytate (inositol-hexaphosphate).

To 1 mL ADJU-PHOS® 2% (w/v) in 5 mM imidazole buffer at pH 7.0, was added concentrated solutions of ATP or AMP to reach final concentrations ranging from 0.2 mM to 5.0 mM. The homogenized suspension (by vigorous shaking) was transferred to a plastic spectrophotometric cuvette and left to sediment for 48 hours until a clear phase separation was observed between the bead of particles and the liquid above. The bed height was measured as a function of the nucleotide concentration. In these conditions, the height of the total volume of suspension in the cuvette was constant and equal to 22 mm. The results are shown in FIG. 10 and FIG. 11.

Experiment No.9 Adsorption of Adenosine Nucleotides to Calcium Phosphate

Figure 12:
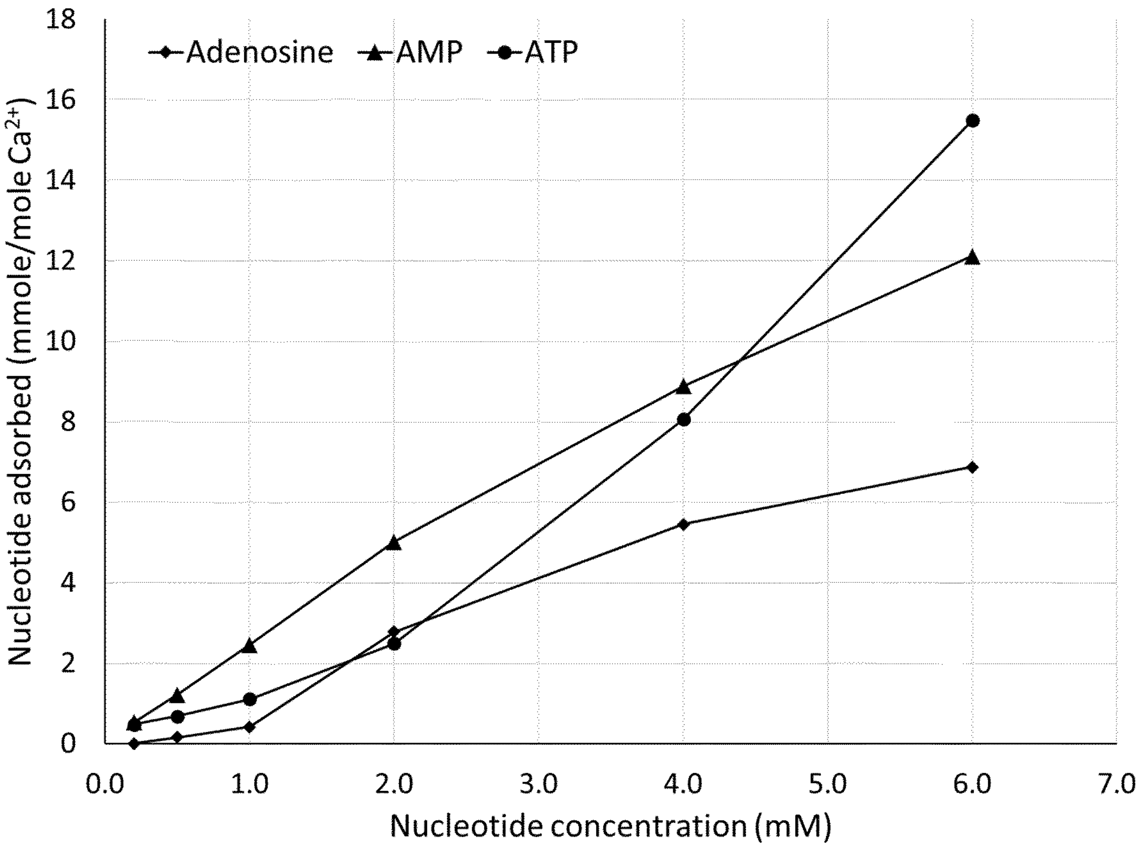
FIG. 12. Adsorption capacity of adenosine, adenosine-5'-monophosphate (AMP) and adenosine-5'-triphosphate (ATP) to Calcium phosphate particles.

Adsorption of adenosine nucleotides to calcium phosphate was investigated by comparing adenosine triphosphate (ATP) to adenosine monophosphate (AMP) and adenosine (A). Calcium phosphate at 1% (w/v) was buffered at pH 7.0 with 5 mM imidazole and blended with solutions of A, AMP and ATP of concentrations ranging from 0.2 mM to 6.0 mM and left to equilibrate for 2 hours at room temperature under agitation to avoid adjuvant particles sedimentation. Adjuvant particles were spun down and Absorbance at 259 nm (Absorbance maximum for adenine) was measured on the supernatants with a spectrophotometer. The amounts of adsorbed nucleotides were calculated from the differences between initial concentrations and final concentrations after adsorption, using a molar extinction coefficient of 15400 cm 1 $M^{-1}$ for adenine. The results are shown in FIG. 12.

Figure 13:
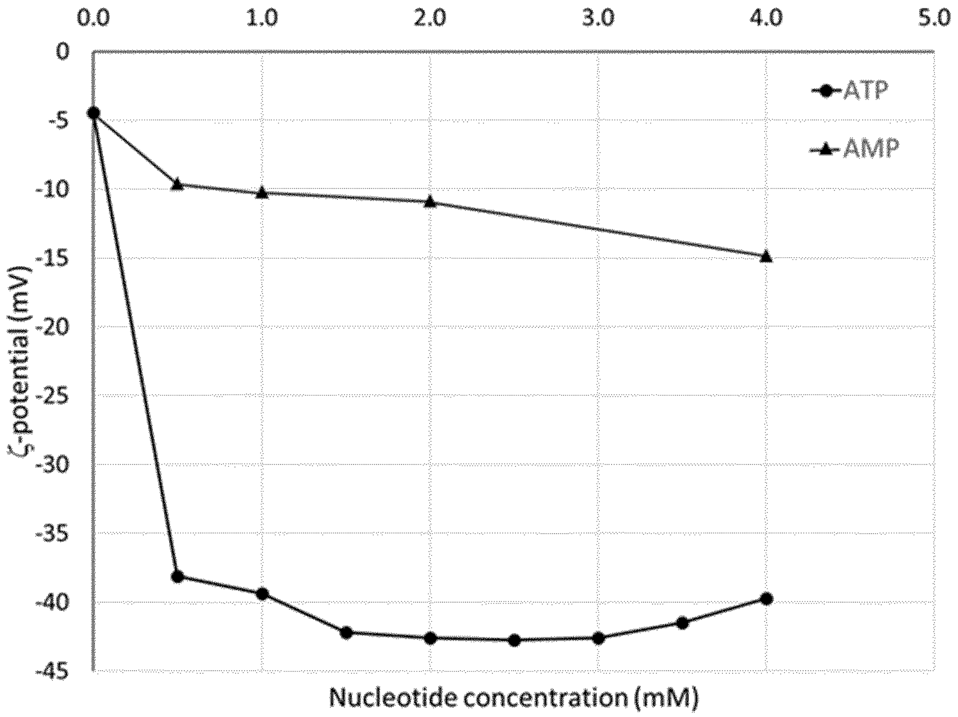
FIG. 13. Effect of adenosine-5'-triphosphate (ATP) and adenosine-5'-monophosphate (AMP) concentration on calcium phosphate ζ-potential.

Experiment No. 10 Effect of Adenosine Nucleotides on Calcium Phosphate Electrostatic ζ-Potential The effect of adenosine nucleotides (ATP and AMP) on calcium phosphate electrostatic ζ-potential was measured by Dynamic Light Scattering (Zeta-Sizer, Nano series, Malvern). ADJU-PHOS® at 0.2% (w/v) in 5 mM imidazole buffer at pH 7.0 and was blended with solutions of ATP or AMP at concentrations ranging from 0.2 mM to 4.0 mM and left to equilibrate for 2 hours at room temperature under agitation to avoid adjuvant particles sedimentation. Samples were transferred into capillary cells (DTS1060, Malvern) and triplicate measurements were performed at 25° C., after 2 minutes of temperature equilibration. The results are shown in FIG. 13.

Experiment No.11 Effect of Adenosine Nucleotides on Calcium Phosphate Sedimentation The effect of adenosine nucleotides (ATP and AMP) on calcium phosphate sedimentation and bed-height was measured. When calcium phosphate is treated with polyphosphates, in the same conditions of pH and salinity, the packing density of the particulate material increases, leading to a reduced bed-height. A higher packing density of calcium phosphate sediment makes the adjuvant particles more difficult to resuspend into the bulk solvent phase, which can become a burden for vaccine manufacturers. Therefore, monitoring the packing density of modified calcium phosphate is an important parameter for downstream applications.

Figure 14:
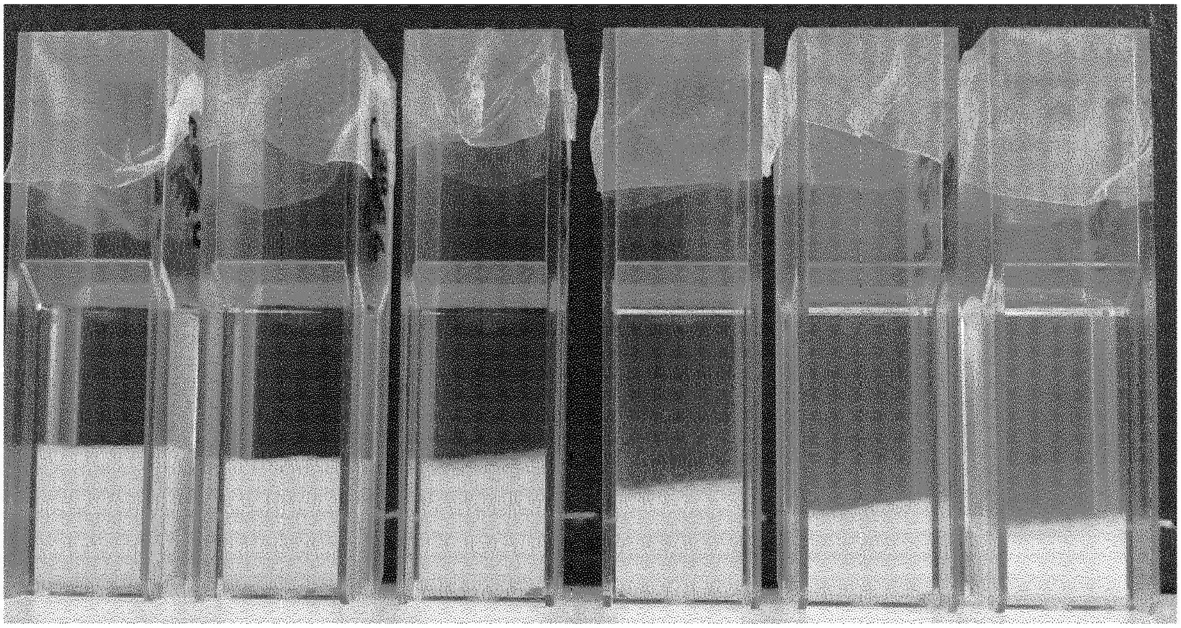
FIG. 14. A photo of homogenized suspensions in plastic spectrophotometric cuvette demonstrating the effect of adenosine-5'-triphosphate (ATP) and adenosine-5'-monophosphate (AMP) concentration on calcium phosphate sediment bed-height. ATP concentrations from left to right: 0.0 mM, 1.0 mM, 2.0 mM, 3.0 mM, 4.0 mM and 5.0 mM.
Figure 15:
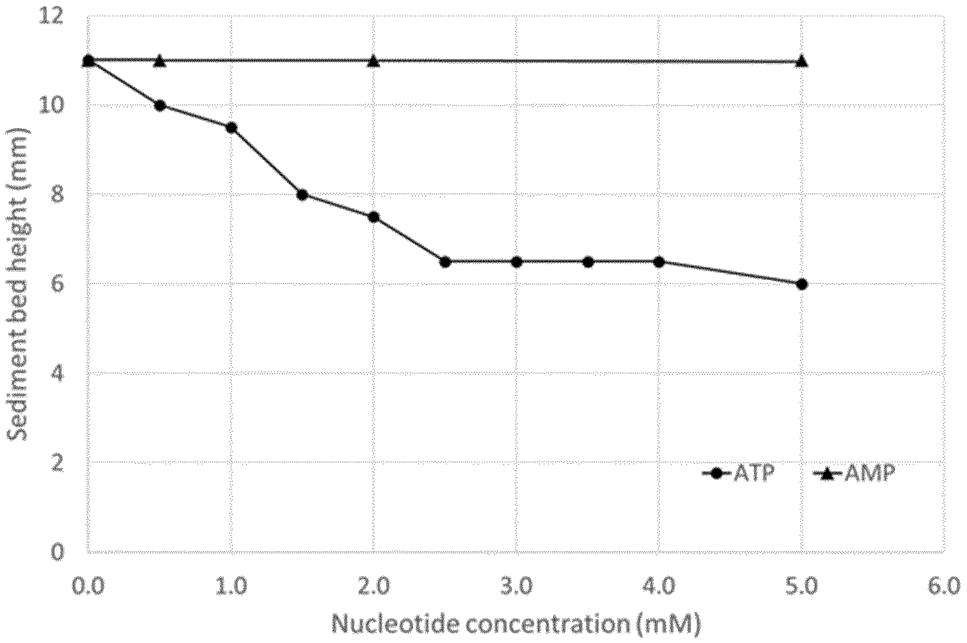
FIG. 15. Effect of adenosine-5'-triphosphate (ATP) and adenosine-5'-monophosphate (AMP) concentration on calcium phosphate sediment bed-height.

To 1 mL calcium phosphate 2% (w/v) in 5 mM imidazole buffer at pH 7.0, was added concentrated solutions of ATP or AMP to reach final concentrations ranging from 0.5 mM to 5.0 mM. The homogenized suspension (by vigorous shaking) was transferred to a plastic spectrophotometric cuvette and left to sediment for 48 hours until a clear phase separation was observed between the bead of particles and the liquid above. The bed height was measured as a function of the nucleotide concentration. In these conditions, the height of the total volume of suspension in the cuvette was constant and equal to 22 mm. The results are shown in FIG. 14 and FIG. 15.

Figure 16:
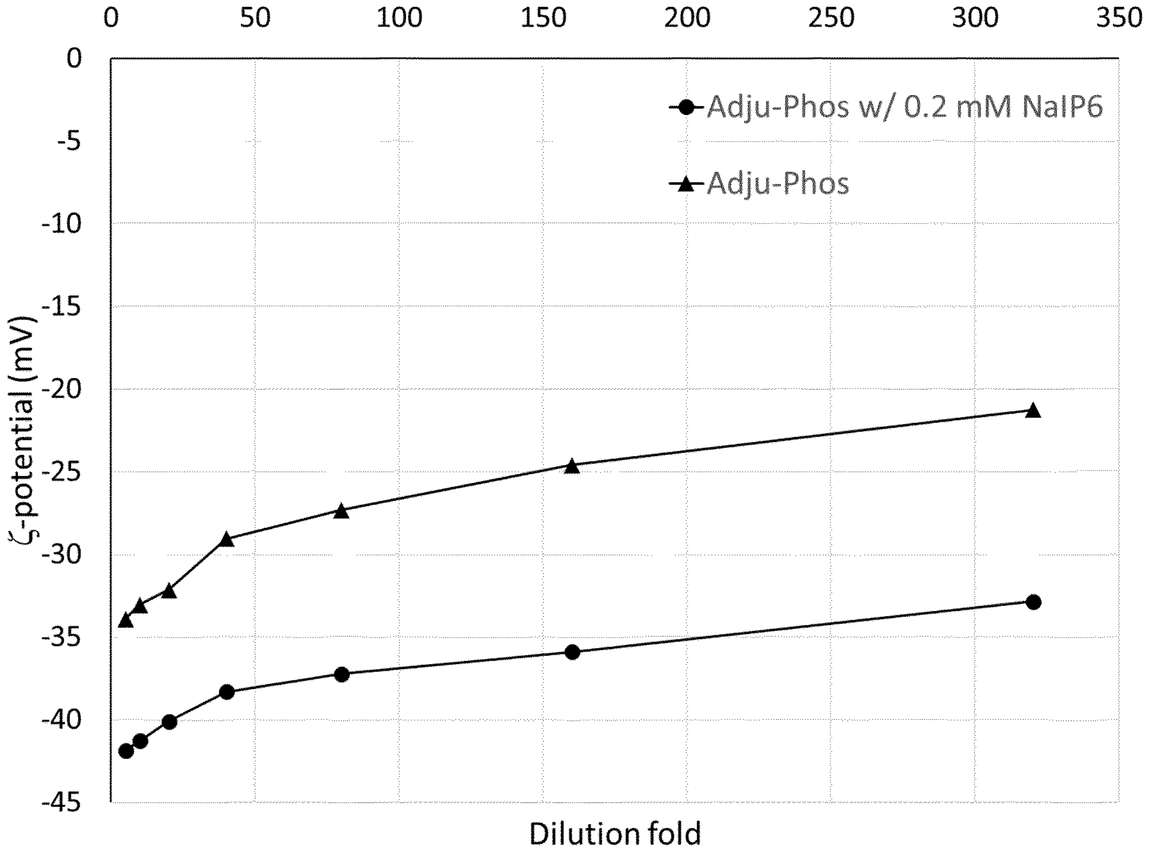
FIG. 16. Effect of serial dilutions of ADJU-PHOS® initially treated with sodium inositol hexa-phosphate.

Experiment No.12 Test for Irreversible Adsorption of IP6 to ADJU-PHOS® Particles In order to test for irreversible adsorption of IP6 to ADJU-PHOS® particles (e.g. through ligand exchange), ADJU-PHOS® at 2% w/v was treated with 0.2 mM Na-IP6 for 24 hours in imidazole buffer 5 mM at pH 7.0. This corresponds to a minimal concentration of IP6 where the ADJU-PHOS® 2-potential reaches its maximum value, in order to limit excess of free, unadsorbed, IP6. The resulting ADJU-PHOS® ZP (modified with IP6) was diluted serially in imidazole buffer 5 mM at pH 7.0, to keep conditions of pH and ionic strength constant. ζ-potential was recorded as a function of the dilution-fold and compared to regular (untreated) ADJU-PHOS®. The results are shown in FIG. 16.

Experiment No.13 Test for Irreversible Adsorption of ATP to ADJU-PHOS®

In order to test for irreversible adsorption of ATP to ADJU-PHOS® particles (e.g. through ligand exchange), an experiment like Experiment no. 12 was conducted. ADJU-PHOS® at 2% w/v was treated with 1.0 mM ATP for 24 hours in imidazole buffer 5 mM at pH 7.0. The resulting ADJU-PHOS® modified with ATP was diluted serially in imidazole buffer 5 mM at pH 7.0, to keep conditions of pH and ionic strength constant. The ζ-potential was recorded as a function of the dilution-fold and compared to regular (untreated) ADJU-PHOS®. The results are shown in FIG. 17.

Experiment No.14 Test for Irreversible Adsorption of IP6 and ATP to Calcium Phosphate In order to test for irreversible adsorption of IP6 or ATP to calcium phosphate particles (e.g. through ligand exchange), an experiment like Experiment nos. 13 and 14 was conducted. Calcium phosphate at 2% w/v was treated with either 0.5 mM IP6 or 1.0 mM ATP for 24 hours in imidazole buffer 5 mM at pH 7.0. The resulting calcium phosphate modified with either IP6 or ATP was diluted serially in imidazole buffer 5 mM at pH 7.0, to keep conditions of pH and ionic strength constant. The ζ-potential was recorded as a function of the dilution-fold and compared to regular (untreated) calcium phosphate. The results are shown in FIG. 18.

Experiment No.15 Large Scale Production Method for ADJU-PHOS® ZP (ADJU-PHOS® Modified with Sodium Inositol Hexaphosphate)

After precipitation and fixation of 45 kg aluminium (III) phosphate hydrate salts in a volume of 2000 L of pure water in a reaction tank, 50 L of a freshly prepared solution of 20 mM dodeca-sodium inositol hexa-phosphate (Na-IP6) in pure water is added to the suspension at a flow-rate of 5 mL/min and under constant stirring. After addition of the complete volume of Na-IP6 solution, the suspension is left under stirring for an additional two hours. The zeta-potential is measured at time intervals, from the start of adding the Na-IP6 solution, to monitor the progress of the adsorption of phytate to the aluminium phosphate particles. Typically, a stable zeta-potential value is reached within the first two hours after addition of the 20 mM Na-IP6 solution. Then, 5.84 kg of NaCl is added to the suspension in order to control the ionic strength as well as the apparent density of the aluminium phosphate particles. The suspension is then transferred to the autoclave tank where ADJU-PHOS® treated with Na-IP6 is sterilized at 121° C. for 30 min, under 1.3 bars of pressure. After cooling-down, the suspension is aseptically packaged in plastic containers for shipping.

Experiment No.16 Comparison of Adjuvant Effect of IP6-Modified ADJU-PHOS® (ADJU-PHOSZP®)-with Regular ADJU-PHOS®

The adjuvant effect of IP6-modified ADJU-PHOS® (ADJU-PHOSZP®) is compared in vivo to regular ADJU-PHOS® and free (non-adjuvanted) antigen as a control, in two different models using female Balb/C mice and hen-egg lysozyme (HEL) as antigen. The experiment is inspired by Majgaard Jensen, O. et al. "On the effect of Al (OH) 3 as an immunulogical adjuvant" APMIS 96, 257-264(1988).

Model 1

In model 1 an amount of HEL is injected s.c. which closely matches the adsorption capacity of ADJU-PHOSZP®. This value can be derived from FIG. 1 hereinabove. Saturation of ADJU-PHOSZP® and regular ADJU-PHOS® is thus achieved (FIG. 1) at a hen-egg lysozyme concentration of 125 μM at which concentration an adsorption capacity of 1.4 and 0.5 mg HEL/mg Al is observed, respectively, for the two adjuvants.

For the in vivo testing two different doses of adjuvant are used: 250 μg Al and 500 μg Al.

Based on the adsorption capacity of 1.4 mg HEL/mg Al for ADJU-PHOSZP® the following amounts of HEL shall be employed in the Model 1 set-up:

For the 250 μg dose an amount of 350 μg HEL is used (250 μg*1.4), and

For the 500 μg dose an amount of 700 μg HEL is used (500 μg*1.4).

These amounts, 350 μg and 700 μg HEL are then tested in three different ways: Adsorbed on 1) ADJU-PHOSZP® 2) Adsorbed on regular ADJU-PHOS® and 3) used non-adjuvanted, i.e. not adsorbed.

Similarly, based on the adsorption capacity of 0.5 mg HEL/mg Al for regular ADJU-PHOS® the following amounts of HEL shall be employed in the Model 2 set-up:

For the 250 μg dose an amount of 125 μg HEL is used (250 μg*0.5), and

For the 500 μg dose an amount of 250 μg HEL is used (500 μg*0.5).

Under the Model 1 conditions the amount of HEL used will be fully adsorbed by the amount of ADJU-PHOSZP®, but only partially by the amount of regular ADJU-PHOS® due to the lower adsorption capacity for this adjuvant. For the 250 μg dose the injection will thus contain (350-125) μg=225 μg unbound antigen when regular ADJU-PHOS® is employed. For the 500 μg dose there will be (700-250) μg=450 μg unbound antigen when regular ADJU-PHOS® is employed. For the control group, all the injected HEL will per definition be unbound.

Model 2

In model 2 an amount of HEL is injected s.c. which closely matches the adsorption capacity of regular ADJU-PHOS®. The values for saturation are calculated under Model 1 above. Two different doses of adjuvant are again used: 250 μg and 500 μg Al, so for the 250 μg dose an amount of 125 μg HEL is used (250 μg*0.5), and for the 500 μg dose an amount of 250 μg HEL is used (500 μg*0.5). These amounts, 150 μg and 300 μg HEL are again tested in three different ways: Adsorbed on 1) ADJU-PHOSZP® 2) Adsorbed on regular ADJU-PHOS® and 3) used non-adjuvanted, i.e. not adsorbed.

Under the Model 2 conditions the amount of HEL used will be fully adsorbed by the amount of ADJU-PHOSZP®, and also by the amount of regular ADJU-PHOS®. However, the full capacity of ADJU-PHOSZP® is not utilized completely under these conditions. This means that the injected dose of ADJU-PHOSZP® will contain free adsorption capacity, which can be expressed as the equivalent amount of HEL. For the 250 μg dose there will thus be a free adsorption capacity equal to (350-125) μg=225 μg HEL on ADJU-PHOSZP®. For the 500 μg dose there will be a free adsorption capacity equal to (700-250) μg=450 μg HEL on ADJU-PHOSZP®. For the control group, there will per definition be no free adsorption capacity.

Testing:

The two models (1 or 2) each contain 3 test groups, each containing 6-8 female Balb/C mice. These are injected s.c with 200 ul containing the following amounts of antigen ("AG") and adjuvant (ADJU-PHOSZP® denoted "ZP", and regular ADJU-PHOS® denoted "AP"):

| 250 μg Al | Model 1 | Model 2 |
| --- | --- | --- |
| Antigen (AG) alone | 350 μg HEL | 125 μg HEL |
| AG + ZP adjuvant | 350 μg HEL | 125 μg HEL |
| AG + AP adjuvant | 350 μg HEL | 125 μg HEL |

-continued

| 500 µg Al | Model 1 | Model 2 |
|---|---|---|
| Antigen (AG) alone | 700 µg HEL | 250 µg HEL |
| AG + ZP adjuvant | 700 µg HEL | 250 µg HEL |
| AG + AP adjuvant | 700 µg HEL | 250 µg HEL |

Anti-HEL antibodies (Ab=IgG) are analyzed after terminal bleeding the mice 21 days after inoculation using an ELISA test for antibodies in serum, as described above. A higher Ab response is observed for the AG+ZP combination than for AG+AP. For the Model 2 a higher Ab response is also observed for the AG+ZP combination than for AG+AP, despite the same amount of antigen injected, indicating that the free adsorption capacity on ADJU-PHOSZP® in the Model 2 set-up could have a positive effect for similar doses of antigen.

Experiment No.17 Comparison of Adjuvant Effect of IP6-Modified Calcium Phosphate (IP6-CAPO) with Regular Calcium Phosphate (CAPO)

This experiment is conducted similarly to Experiment no.15 hereinabove. Saturation of IP6-CAPO and regular CAPO is achieved (see FIG. 3) is reached at an adsorption capacity of 175 µg HEL/mg Ca and 40 µg HEL/mg Ca, respectively. With these values for saturation the following amounts of antigen (HEL) to be injected can be calculated analogously to Exp.15 hereinabove:

| 250 µg Ca | Model 1 | Model 2 |
|---|---|---|
| Antigen (AG) alone | 44 µg HEL | 10 µg HEL |
| AG + IP6-CAPO adjuvant | 44 µg HEL | 10 µg HEL‡ |
| AG + CAPO adjuvant | 44 µg HEL* | 10 µg HEL |
| **500 µg Ca** | **Model 1** | **Model 2** |
| Antigen (AG) alone | 88 µg HEL | 20 µg HEL |
| AG + IP6-CAPO adjuvant | 88 µg HEL | 20 µg HEL‡ |
| AG + CAPO adjuvant | 88 µg HEL* | 20 µg HEL |

For Model 1: With the above amounts there will be unbound antigen* on CAPO. For the 250 µg dose injected Ca, this will amount to (44-10) µg=34 µg antigen. For the 500 µg dose injected Ca, the unbound amount of antigen will be 88−20=68 µg antigen.

For Model 2: With the above amounts there will be free capacity' on IP6-CAPO. For the 250 µg dose injected Ca, this will amount to 44−10=34 µg antigen, and for the 500 µg dose injected Ca, this will amount to 88−20=68 µg antigen.

Testing:

The in vivo testing of the two models (1 or 2) is conducted as for Experiment 15 hereinabove.

Each model contains 3 test groups, each containing 6-8 female Balb/C mice. These are injected s.c with 200 µl containing the following amounts of antigen ("AG") and adjuvant (IP6-CAPO denoted "CAPO*", and regular calcium phosphate denoted "CAPO"):

| 250 µg Ca | Model 1 | Model 2 |
|---|---|---|
| Antigen (AG) alone | 44 µg HEL | 10 µg HEL |
| AG + CAPO* adjuvant | 44 µg HEL | 10 µg HEL |
| AG + CAPO adjuvant | 44 µg HEL | 10 µg HEL |
| **500 µg Ca** | **Model 1** | **Model 2** |
| Antigen (AG) alone | 88 µg HEL | 20 µg HEL |
| AG + CAPO* adjuvant | 88 µg HEL | 20 µg HEL |
| AG + CAPO adjuvant | 88 µg HEL | 20 µg HEL |

Anti-HEL antibodies (Ab=IgG) are analyzed after terminal bleeding the mice 21 days after inoculation using an ELISA test for antibodies in serum, as described above. A higher Ab response is observed for the AG+CAPO* combination than for AG+CAPO. For the Model 2 a higher Ab response is also observed for the AG+CAPO* combination than for AG+CAPO, despite the same amount of antigen injected, indicating that the free adsorption capacity on IP6-modified Cacium phosphate (IP6-CAPO, CAPO*) in the Model 2 set-up could have a positive effect for similar doses of antigen.

The invention claimed is:

1. Organically-derivatized mineral micro-particles comprising mineral micro-particles derivatized by one or more organic polyphosphates, wherein the mineral micro-particles are selected from aluminum phosphate and amorphous aluminum hydroxyphosphate micro-particles having a size in a range from 0.01 µm to 10 µm, wherein the one or more organic polyphosphates is selected from compounds of formula 1A or 1B Formula 1A

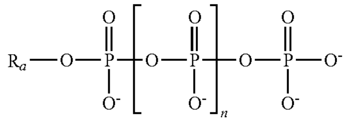

Formula 1B

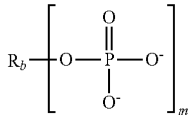

wherein:

n is an integer in the range of 1-5;

m is an integer in the range of 2-10;

$R_a$ denotes adenosine; and $R_b$ denotes organic substituents selected from inositols and other cyclitols, wherein a stoichiometric ratio of aluminum (Al) to phosphorus (P) is 1.2+/−0.15 to 1, and wherein an antigen is adsorbed on a surface of at least a portion of the organically-derivatized mineral-microparticles.

2. The organically-derivatized mineral micro-particles according to claim 1, wherein the one or more organic polyphosphates comprises an inositol phosphate selected from inositol bisphosphate (IP2), inositol trisphosphate (IP3), inositol tetraphosphate (IP4), inositol pentakisphosphate (IP5) and inositol hexaphosphate (IP6).

3. The organically-derivatized mineral micro-particles according to claim 1, wherein the one or more organic polyphosphates comprises inositol hexaphosphate (IP6) or a salt thereof.

4. The organically-derivatized mineral micro-particles according to claim 1, wherein the microparticles are present in a medicinal product.

5. The organically-derivatized mineral micro-particles according to claim 1, wherein the micro-particles are present in a biomolecules delivery or adsorption system.

6. The organically-derivatized mineral micro-particles according to claim 5, wherein the biomolecules delivery system is a vaccine adjuvant.

7. The organically-derivatized mineral micro-particles according to claim 6, wherein the vaccine adjuvant is a vaccine.

8. The organically-derivatized mineral micro-particles according to claim 5, wherein the biomolecules delivery system includes blood fractionation.

9. A biomolecules delivery or adsorption system comprising the organically-derivatized mineral micro-particles according to claim 1.

10. The biomolecules delivery or adsorption system according to claim 9, wherein the biomolecules delivery system is a vaccine adjuvant.

* * * * *